United States Patent [19]

Clive et al.

[11] Patent Number: 5,410,033
[45] Date of Patent: Apr. 25, 1995

[54] DEOXYGENATION OF CIS VICINAL DIOLS TO MAKE DIDEHYDRO DIDEOXY NUCLEOSIDIES AND SYNTHETIC INTERMEDIATES

[75] Inventors: Derrick L. J. Clive; Philip L. Wickens, both of Edmonton, Canada

[73] Assignee: Terochem Laboratories Limited, Edmonton, Canada

[21] Appl. No.: 12,828

[22] Filed: Feb. 3, 1993

[51] Int. Cl.$^6$ ............... C07H 19/073; C07H 19/173
[52] U.S. Cl. ............................. 536/27.14; 536/27.62; 536/28.2; 536/28.5; 536/28.53; 568/704
[58] Field of Search ................ 536/27.14, 28.2, 27.62, 536/28.5, 28.53; 568/704

[56] References Cited

U.S. PATENT DOCUMENTS 4,008,287 2/1977 Verbrugge et al. ............ 200/648 D
4,450,290 5/1984 Sanderson et al. ................ 560/246

FOREIGN PATENT DOCUMENTS 0348170 12/1989 European Pat. Off. ............... 514/43

OTHER PUBLICATIONS

Clive, D. L. J., et al., 1993. "Reaction of cis-Vicinal Dimethanesulfonates with Te$^{2-}$ ...", Journal of Chemical Society, Chemical Communications, No. 11, 7 Jun. 1993, Letchworth GB, pp. 923–924.

Clive, D. L. J., et al., 1980. "Alkali Metal O,O-Diethyl Phosphorotelluroates, a Reagent Class for Deoxygenation of Epoxides, Especially Terminal Epoxides", Journal of Organic Chemistry, vol. 45, No. 12, 6 Jun. 1980, Easton US, pp. 2347–2354.

Cosford, N. D. P., et al., 1991. "Selenium Nucleophiles for the Preparation of Antiviral Nucleosides", vol. 56, No. 6, 15 Mar. 1991, Easton US, pp. 2161–2165.

Prince, M., et al., 1966. "Sodium Selenide Vicinal Dihalide Elimination", vol. 31, No. 12, Dec. 1966, Easton US, pp. 4292–4293.

Clive, D. L. J., et al., 1982, "New Method for Coupling Allyl Halides: Use of Te$^{2-}$ Species", vol. 47, No. 9, 23 Apr. 1982, Easton US, pp. 1641–1647.

Johnson, R., et al., 1992. "Derivatives of 2',3'-Dithiouridine and (1-B-D-(2,3-Dithioxylofuranosyl)-)Uracil", vol. 33, No. 52, 22 Dec. 1992, Oxford GB, pp. 8151–8154.

Thiem, J., et al., 1985, "Synthesis and Perkow Reaction of Uridinen Derivatives", vol. 4, No. 4, 1985, pp. 487–506.

Tsujino, J., et al., 1989. "A Process for Preparation of 2'-Bromo-2',3'-Didehydro-2',3'-Dideoxycytidine as an Intermediate for 2',3'-Dideoxycytidine", vol. 111, No. 9, 28 Aug. 1989, Columbus, Ohio, US; abstract No. 78553n, p. 803, col. 1.

Haraguchi et al.(I), "Preparation and Reactions of 2'- and 3'-Vinyl Bromides of Uracil-Nucleosides: Versatile Synthons for Anti-HIV Agents", *Tett. Lett.*, 32(28), 3391–3394 (1991).

Haraguchi et al.(II), "Nucleosidic Enol Esters: A Versatile Tool for the Synthesis of 3'-Carbon-Substituted Nucleosides", *Tett. Lett.*, 32(6), 777–780 (1991).

Wrensford et al., "Synthesis of 3-Bromo-6-ethenyltetrahydro-2,2,6-trimethyl-2H-pyran", *Tett. Lett.*, 31(10), 4257–4260 (1991).

T. W. Greene and P. G. M. Wuts, *Protective Groups in Organic Synthesis*, 2nd Ed., Wiley, 1991; Ch. 2, pp. 11–14; Ch. 3, pp. 143–144; Ch. 7, pp. 309–315.

(List continued on next page.)

Primary Examiner—John W. Rollins
Assistant Examiner—L. Eric Crane
Attorney, Agent, or Firm—Millen, White, Zelano & Branigan

[57] ABSTRACT

Cis vicinal diols are converted to olefins using tellurides or selenide reagents. The diol is reacted to convert the hydroxyl groups into good leaving groups for nucleophilic substitution. Alkyl and aryl sulfonate groups such as mesylate or tosylate are preferred. The product is then reacted with a source of Te$^{2-}$ or Se$^{2-}$ ions, preferably an alkali metal telluride or selenide, to form the desired olefin. The process is particularly useful for generating 2',3'-unsaturation in the sugar moiety of nucleosides. Novel intermediate mesylate, tosylate and olefin derivatives of nucleosides are also provided.

28 Claims, 1 Drawing Sheet

OTHER PUBLICATIONS

"Tellurium", W. C. Cooper, Ed., Van Nostrand Reinhold, New York, 1971, pp. 188, 274–280.

M. Sekine et al., *J. Org. Chem.*, 1990, 55, 924–928.

"Selenium", R. A. Zingaro et al., Eds, Van Nostrand Reinhold, New York, 1974, pp. 438–439, 530–545.

E. Block, Org. Reacts., 1984, 30, 457.

Chemical and Engineering News, 1991, Oct. 14, p. 17.

"Naming and Indexing of Chemical Substances for Chemical Abstracts, A Reprint of Appendix IV to 1982 Index Guide", A. Chem. Soc. para 203.

L. I. Fieser et al., Reagents for Organic Synthesis, vol. 1, Wiley, New York, 1967, pp. 662–664.

A. B. Harvey et al., J. Chem. Phys., 1969, 50, 4949–4961.

M. M. Mansuri et al., J. Org. Chem. 1989, 54, 4780–4785.

B. Kaskar et al., J. Heterocyclic Chem., 1989, 26, 1531–1533.

T. Yamaguchi et al., Nucleosides and Nucleotides, 1992, 11, 373–382.

P. Kumar et al., Nucleosides and Nucleotides, 1992, 11, 401.

G. Brauer, Ed. "Handbuck der Praparativen Anorganischem Chemie", Ferdinand Enke: Stuttgart, 1975; vol. I, p. 431.

J. B. Lambert et al., J. Org. Chem., 1979, 44, 1480–1485.

H. A. Shonle et al., J. Am. Chem. Soc., 1921, 43, 361–365.

M. Kawana et al., Bull. Chem. Soc. Jpn., 1981, 54, 1492–1504.

Taniguchi et al., Tetrahedron 1974, 30, 3574–3552.

K. Koga et al., Tetrahydron Lett. 1971, 263–266.

Codington et al., J. Org. Chem., 1964, 29, 558.

R. S. Tipson et al., Ed. "Synthesis Procedures in Nucleic Acid Chemistry", Wiley, 1968, vol. I, pp. 441–442.

J. J. Fox et al., J. Am. Chem. Soc., 1957, 79, 2775–2778.

N. D. P. Cosford et al., J. Org. Chem., 1991, 56, 2161–2165.

D. M. Brown et al., J. Chem. Soc., 1956, 2384–2387.

H. U. Blank et al., Justus Leibigs Ann. Chem., 1970, 742, 16–28.

H. P. M. Fromageot et al., Tetrahedron, 1967, 23, 2315–2331.

Y. Amino et al., Bull. Chem. Soc., 1991, 64, 620–623.

R. Vinayak et al., Nucleic Acids Research, 1992, 20, 1265–1269.

Aldrich Chemical Co., J. Org. Chem., Dec. 1990, 55, #25 (Back Cover).

P. Prince et al., J. Org. Chem., 1966, 31, 4292–4293.

L. Engman, Tetrahedron Lett., 1982, 23, 3601–3602.

T. K. Raja, Indian J. Chem., 1980, 19B, 812–813.

D. Clive et al., J. Org. Chem., 1980, 45, 2347–2354.

IUPAC Nomenclature of Organic Chemistry, Sections A, B, C, D, E, F and H, 1979, Pergamon Press, Oxford.

D. Clive et al., J. Org. Chem., 1982, 47, 1641–1647.

M. Sekine et al., J. Org. Chem., 1990, 55, 924–928.

2',3'-dideoxyadenosine (DDA)

3'-deoxy-2',3'-didehydrothymidine (D4T)

2',3'-dideoxyinosine (DDI)

2',3'-dideoxycytidine (DDC)

5,410,033

DEOXYGENATION OF CIS VICINAL DIOLS TO MAKE DIDEHYDRO DIDEOXY NUCLEOSIDIES AND SYNTHETIC INTERMEDIATES

FIELD OF THE INVENTION

The present invention is directed to a process for converting cis vicinal diols into olefins. The invention is also directed to novel nucleoside derivatives which are formed as intermediates in the process.

BACKGROUND OF THE INVENTION

Deoxygenation of cis vicinal diols into olefins, especially in natural products, nucleosides, antibiotics and carbohydrates, is a challenge. Efficient and mild methodologies, compatible with other sensitive functional groups and ring systems, are needed. (see E. Block, Org. Reacts., 1984, 30, 457).

A good summary of deoxygenation techniques for converting vicinal diols to unsaturated systems was published by Aldrich Chemical Co., J. Org. Chem., December 1990, #25. Included are the Corey-Winter and Eastwood methods, which generate a carbene intermediate, the Barton-McCombie method, which uses free radical fragmentation of bis-xanthates with tributyltin hydride or with certain silanes, and the Robins-Moffatt method which uses an α-acetoxyisobutyroyl bromide reagent.

The conversion of 1,2-dibromides into olefins with tellurium or sellurium compounds has been reported (see P. Prince et al., J. Org. Chem., 1966, 31, 4292; L. Engman, Tetrahedron Lett., 1982, 23, 3601, and T. K. Raja, Indian J. Chem., 1980, 19B, 812). However, the preparation of vicinal dibromides is generally not simple. Olefins are commonly protected as dibromides, thus necessitating debromination by the above techniques.

Deoxygenation of nucleosides has recently received a great deal of attention. Acquired immunodeficiency (AIDS) is a consequence of infection by the human immunodeficiency virus (HIV). Several 2',3'-dideoxynucleosides have been shown to be effective in the treatment of cells infected with HIV. One compound, 3'-azido-3'-deoxythymidine (AZT), has been approved by the FDA in the United States for the treatment of individuals with AIDS. 2',3'-Dideoxyinosine (DDI) has recently received FDA approval for use in patients for whom AZT is no longer effective (Chem. and Eng. News, 1991, Oct. 14, p.17). These, and related nucleoside derivatives, are believed to inhibit viral reverse transcriptase by competing with the natural substrates at the nucleotide binding site on the enzyme, and the modified nucleosides are incorporated into proviral DNA, which then stops growing. Other nucleosides of interest in respect of their activity against HIV include the unsaturated nucleoside 1-(2,3-dideoxy-β-D-glyceropent-2-enofuranosyl)thymine, (D4T) also known as 2',3'-dideoxy-2',3'-didehydro-5-methyluridine, 2',3'-dideoxyadenosine (DDA), and 2',3'-dideoxycytidine (DDC). D4T has been reported to have a comparable potency with AZT against HIV in culture.

Various approaches for an efficient preparation of D4T and related compounds are under investigation (see Mansuri, M et. al., J. Org. Chem. 1989, 54, 4780). Cosford et al. (J. Org. Chem., 1991, 56, 2161), report the preparation of several thymidine derivatives with nucleophilic selenium reagents to produce, after selenoxide elimination, the desired unsaturation at the 2',3'-position in the sugar moiety of the nucleosides.

In spite of considerable effort in this area there is still a need for a mild, efficient method for converting cis vicinal diols into olefins, particularly for the introduction of 2',3', -unsaturation in the sugar moiety of nucleosides

SUMMARY OF THE INVENTION

The inventor discovered that cis vicinal diols can be converted to olefins in very high yield, under mild conditions, using telluride or selenide reagents. In accordance with the process of this invention, a cis vicinal diol is reacted to convert the hydroxyl groups into good leaving groups for nucleophilic substitution. Leaving groups which replace the hydroxyl hydrogen but which leave the hydroxyl oxygen intact are used. Particularly preferred leaving groups are alkyl or aryl sulfonate groups such as mesylates and tosylates. The product is then reacted with a source of $Te^{2-}$ or $Se^{2-}$, preferably an alkali metal telluride or selenide, to form the desired olefin.

The process is particularly suited for generating 2',3'-unsaturation in the sugar moiety of nucleosides.

It should be understood that the term cis vicinal diols is meant to include hydrocarbon substructures with hydroxyl groups on adjacent C-atoms, the hydroxy groups being either in a cis relationship or being able to adopt a cis relationship during the reaction, as discussed more fully hereinafter.

Without being bound by the same, it is believed that the reaction proceeds via the generation of an epitelluride or episelenide intermediate as shown in equation 1 (with the leaving groups being illustrated by mesylate groups (OMs):

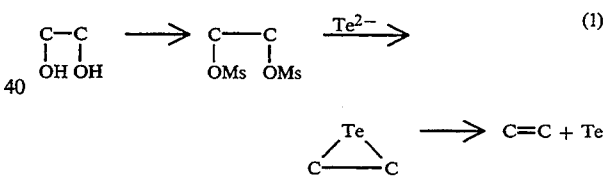

(See D. Clive et al., J. Org. Chem., 1980, 345, 2347, the epitellurides being generated by different techniques).

DESCRIPTION OF THE PREFERRED EMBODIMENTS

Figure 1B:
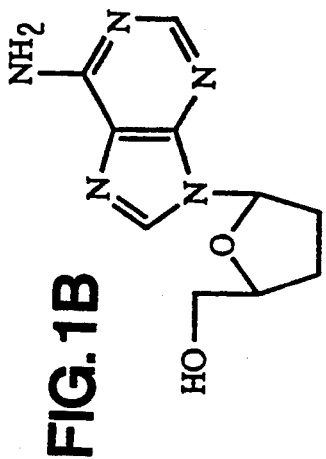
FIG. 1 is a formula sheet of representative dideoxy nucleosides.

Generally, any cis vicinal diol compound may be converted to an olefin by the process of this invention. For cyclic structures, cis vicinal diols are those diols having a pair of hydroxyl groups on adjacent carbons of the ring and that are on the same side of the reference plane (adapted from "Naming and Indexing of Chemical Substances for Chemical Abstracts, A Reprint of Appendix IV to 1982 Index Guide", A. Chem. Soc., para 203. See also IUPAC Nomenclature of Organic Chemistry, Sections A,B,C,D,E,F and H, 1979, Pergamon Press, Oxford). Cis vicinal diol groups may be present in a wide range of hydrocarbons, including straight chain or branched alkanes and cycloalkanes. These hydrocarbon units may contain double and/or triple bonds and/or heteroatoms. Aryl and heteroaryl units may also be present. Any of these hydrocarbon, aryl or heteroaryl units may contain substituents and other functional groups such as ester, carbonyl or amide groups. Aliphatic bromide and iodide units should be avoided. Particularly important cis vicinal diols are natural products, such as nucleosides, antibiotics and carbohydrates. If other reactive functional groups (ie. apart from the vicinal diol groups) such as nitrogen atoms (especially in the form of primary or secondary amines) or oxygen atoms (especially as alcohols or phenols) are present, in the diol, these can be N- or O-protected, by procedures and protecting groups which are known in the art. For instance, nitrogen may be protected by conversion to aliphatic or aromatic amide groups or by benzylation. Oxygen may be protected by conversion to aliphatic or aromatic ester groups, or by silylation or benzylation. Exemplary protecting groups are (a) for nitrogen—acetamides, benzamides, (dimethylamino)methylene and silyl, and (b) for oxygen—acetates, benzoates, trityl (triphenylmethyl), dimethoxytrityl [bis (4-methoxylphenyl) phenylmethyl], and silyl. Other reactive functional groups can be protected, for example sulphur can be protected as esters and phenolic hydroxyl groups may be protected as methyl ethers or esters such as acetates. Numerous protecting groups for oxygen and nitrogen are given in Greene and Wuts (T. W. Greene and P. G. M. Wuts, Protective Groups in Organic Synthesis, 2d Ed., Wiley, 1991).

In accordance with the process of this invention, cis vicinal diols are first reacted to convert the adjacent hydroxyl groups into good leaving groups for nucleophilic substitution. Leaving groups which replace the hydroxyl hydrogen but leave the hydroxyl oxygen intact are used. Particularly preferred leaving groups are alkyl or aryl sulfonates. The alkyl group is typically a $C_1$–$C_{16}$ alkyl group which is branched, straight chain or cyclic and which may contain or carry non reactive substituents, for instance halides such as chloro, fluoro, alkoxy, aryloxy, alkyl esters, carboxamides [CONR',R" where R',R"=H, alkyl, aryl, heteroaryl], alkylthio, arylthio, aralkylthio, heteroarylthio, alkylamino, cycloalkylamino, aralkylamino, arylamino or heteroarylamino. The aryl group is typically a $C_6$–$C_{16}$-aryl group, which may contain and carry non reactive substituents such as those set out for alkyl sulfonates. Non reactive substituents include those substituents which will not undergo nucleophilic displacement by reaction with the telluride or selenide ions. Particularly preferred alkyl or aryl sulfonates are tosylates and mesylates. Other leaving groups include trifluoromethane sulfonate (triflate), benzenesulfonate and, p-nitrobenzenesulfonate.

Generation of a mesylate or tosylate leaving groups is accomplished by known techniques, see for example L. I. Fieser et al., Reagents for Organic Synthesis, Vol. 1, Wiley, New York, 1967, p. 662. In general, the diol is reacted with methanesulfonyl chloride or p-toluenesulfonyl chloride and an organic base such as triethylamine or pyridine, in an inert solvent, such as dichloromethane, ether, tetrahydrofuran, and chloroform. The reaction is preferably commenced at a low temperature (about 0° C.) and the mixture is allowed to warm to room temperature.

The converted diol is then reacted with a source of $Te^{2-}$ or $Se^{2-}$ to form the olefin. Preferably the telluride or selenide is provided as an alkali or alkaline earth metal salt (eg. Na, Li, K, Mg, and Ca). Sodium or lithium compounds are particularly preferred. Preparation of such compounds is by methods known in the art, (see "Tellurium" W. C. Cooper, Ed, Van Nostrand Reinhold, New York, 1971; "Sellenium" R. A. Zingaro et al, Eds, Van Nostrand Reinhold, New York, 1974). The Li compounds are preferably generated in situ from metallic Te or Se and lithium triethylborohydride (Super-Hydride, trade mark of Aldrich Chemical Co., Inc.) as described by D. Clive et al., J. Org. Chem., 1982, 47, 1641. The Na compounds are preferably prepared from sodium metal and elemental Te or Se in liquid ammonia (see G. Brauer, "Handbuch der Präparativen Anorganischen Chemie", F. Enke, Stuttgart, 1975, Vol. I, 431; A. B. Harvey et al., J. Chem. Phys. 1969, 50, 4949).

The reaction between the alkali metal telluride or selenide is performed under mild conditions (preferably room temperature) in a solvent in which the organic starting materials have some solubility. Ethereal solvents such as tetrahydrofuran (THF) and dioxane or acetonitrile are preferred, although alcoholic solvents such as ethanol may also be used. An inert atmosphere is preferred in order to avoid premature oxidation of the selenium or tellurium species.

Once the desired olefin product is obtained, the protecting groups may be removed by well known techniques. For instance methods of removing 5'-O-trityl groups and N-acetyl groups are discussed in M. M. Mansuri et al., J. Org. Chem. 1989, 54, 4780, N. D. P; Cosfard et al., J. Org. Chem., 1991; 56, 2161; B. Kaskar et al., J. Heterocyclic Chem., 1989, 26, 1531; and M. Sedine et al., J. Org. Chem., 1990, 55, 924.

Hydrogenation of the olefin, particularly in respect of the nucleoside olefin products, also proceeds by well known techniques such as with hyrogen/Pd/charcoal.

The process has been demonstrated with naturally occuring purine and pyrimidine nucleosides (O- and N-protected as appropriate). However, it should be understood that the process will also work for nucleosides in which the bases have been modified. Exemplary base-modified nucleic acids relevant to the treatment of AIDS are described in T. Yamaguchi et al., Nucleic Acids and Nucleotides, 1992, 11,373 and P. Kumar et al., Nucleic Acids and Nucleotides, 1992, 11, 401. Thus the term "nucleoside", as used herein and in the claims is meant to include those with natural or modified bases.

Figure 1D:
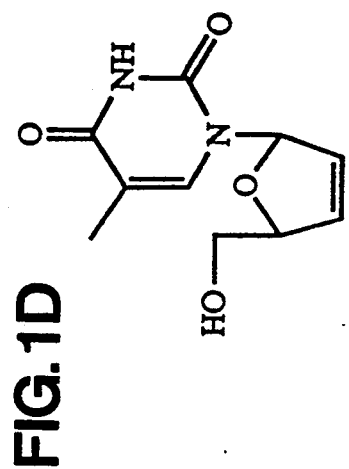
Figure 1A:
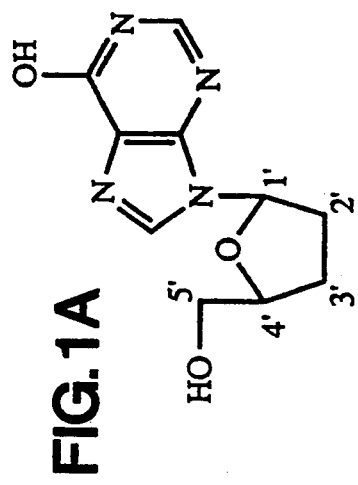
Figure 1C:
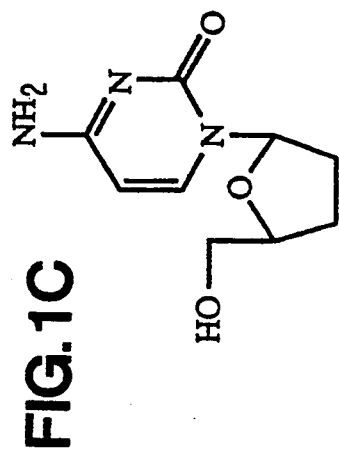

Exemplary saturated and unsaturated nucleosides relevant to AIDS treatment are shown in FIG. 1.

The invention is further illustrated by the following non-limiting examples.

EXAMPLES

In the examples, compounds isolated by flash chromatography were homogeneous by TLC and, unless otherwise stated, were pure as judged by high field $^1$H NMR spectra.

Example 1

(a) Preparation of Sodium Telluride ($Na_2Te$)

A three-necked round-bottomed flask was charged with tellurium powder (200 mesh, 2.2053 g, 17.28 mmol) and a stirring bar. Sodium (0.7947 g, 34.57 mmol) was placed in a side-arm addition tube, and the central neck of the flask was fitted with a condenser charged with dry-ice/acetone and closed by a septum carrying both an entry needle for argon and an exit needle leading to an oil bubbler. The third neck of the flask was temporarily closed by a septum and the flask was flushed with argon. The septum in the third neck was removed and immediately replaced by an adaptor (fitted with a tap) connected to a tank of liquid ammonia. The flask was now cooled with dry ice/acetonitrile and ammonia was led in until ca. 200 mL had collected. The ammonia inlet was closed and a slow purge of argon was maintained. The stirrer was started and the sodium was added portionwise by tapping the side-arm addition tube. The mixture changed from red to bluish-green to white, by which stage formation of sodium telluride was complete. The cooling bath was removed from beneath the flask, and stirring was continued overnight, during which period the coolant in the condenser attained room temperature and the ammonia evaporated. The resulting beige sodium telluride (ca. 100% yield) was transferred in an argon-filled glove bag to a storage flask. (Cf. G. Brauer, Ed. "Handbuch der Präparativen Anorganischen Chemie", Ferdinand Enke: Stuttgart, 1975; Vol. I, p.431; A. B. Harvey et al., J. Chem. Phys. 1969, 50, 4949).

(b) Preparation of Sodium Selenide ($Na_2Se$)

A three-necked round-bottomed flask was charged with selenium powder (325 mesh, 2.8476 g, 36.0657 mmol) and a stirring bar. Sodium (1.7412 g, 75.7380 mmol) was placed in a side-arm addition tube, and the central neck of the flask was fitted with a condenser charged with dry-ice/acetone and closed by a septum carrying both an entry needle for argon and an exit needle leading to an oil bubbler. The third neck of the flask was temporarily closed by a septum and the flask was flushed with argon. The septum in the third neck was removed and immediately replaced by an adaptor (fitted with a tap) connected to a flask containing a small amount (ca. 1 g) of sodium (to remove the water). This latter flask was in turn connected to a tank of liquid ammonia and was then cooled with dry-ice/acetonitrile. Ammonia was led in until ca. 200 mL had collected. The cooling bath was removed and the ammonia was transferred to the reaction vessel which was cooled with dry-ice/acetonitrile. The ammonia inlet was closed and a slow stream of argon was maintained. The stirrer was started and the sodium was added portionwise by tapping the side-arm addition tube. The mixture changed color and eventually became white, by which stage formation of sodium selenide was complete. The cooling bath was removed and stirring was continued overnight, during which period the coolant in the condenser attained room temperature and the ammonia evaporated. The resulting slightly orange sodium selenide (ca. 100% yield) was transferred in an argon-filled golve bag to a storage flask.

Example 2

Preparation of 1-(3-butenyl)napthalene (a) 4-(1-naphthyl)-1,2-butanediol

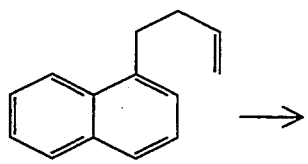

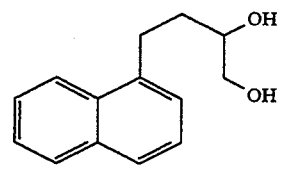

Osmium tetroxide (1.7 mL, 2.5% w/w solution of $OsO_4$ in t-BuOH) was added to a stirred solution of 1-(3-butenyl)naphthalene (See J. B. Lambert et al., J. Org. Chem., 1979, 44, 1480) (1.1215 g, 6.1533 mmol) and 4-methylmorpholine-N-oxide (1.0331 g, 7.6526 mmol) in acetone (30 mL) and water (15 mL). Stirring at room temperature was continued for 43 h. EtOAc (100 mL) was then added and the organic layer was washed with water (1×100 mL) and 10% aqueous $Na_2SO_3$ (2×50 mL). The organic extract was dried ($MgSO_4$) and evaporated. Flash chromatrography of the residue over silica gel (5×20 cm), using 70% EtOAc in hexane, gave the diol (1.2004 g, 90%): FTIR ($CH_2Cl_2$ cast) 3360 cm$^{-1}$; $^1$H NMR ($CDCl_3$, 200 MHZ) δ 1.70–2.05 (m, 4H), 3.05–3.45 (m, 2H), 3.50 (dd, J=7, 11 Hz, 1H), 3.71 (dd, J=3, 11 Hz, 1H), 3.75–3.95 (m, 1H), 7.30–7.60 (m, 4H), 7.60–7.80 (m, 1H), 7.80–8.20 (m, 1H); $^{13}$C NMR ($CDCl_3$, 75.469 MHz) δ 28.93, 34.02, 66.86, 71.89, 123.74, 125.55, 125.58, 125.92, 126.07, 126.82, 128.85, 131.81, 133.97, 137.89; exact mass, m/z calcd for $C_{14}H_{16}O_2$ 216.1151, found 216. 1151.

(b) 4-(1-Naphthyl)butane-1,2-diol dimethanesulfonate

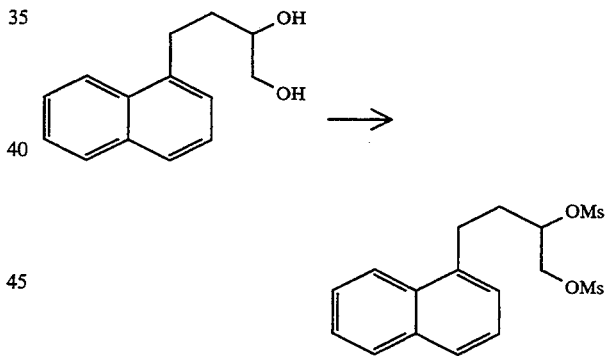

Methanesulfonyl chloride (1.60 mL, 20.77 mmol) in $CH_2Cl_2$ (10 mL) was added dropwise to a stirred and cooled (0° C.) solution of 4-(1-naphthyl)-1,2-butanediol (1.1229 g, 5.192 mmol) and pyridine (3.4 mL, 41.54 mmol) in $CH_2Cl_2$ (10 mL) (argon atmosphere). The ice bath was removed and stirring was continued for 16 h. The mixture was poured onto ice (ca. 50 g) and extracted with EtOAc (1×100 mL). The organic extract was washed with 10% aqueous $CuSO_4$ (2×50 mL) , dried ($MgSO_4$) and evaporated. Flash chromatography of the residue over silica gel (3×30 cm) , using 50:50 EtOAc-hexane, gave the dimesylate (1.8493 g, 96%): FTIR ($CH_2Cl_2$ cast) 1356, 1173 cm$^{-1}$; $^1$H NMR ($CDCl_3$, 200 MHz) δ 2.05–2.40 (m, 2H), 3.0–3.10 (s, 3 H), 3.10–3.15 (s, 3 H), 3.15–3.45 (m, 2H), 4.30 (dd, J=6, 11 Hz, 1H), 4.44 (dd, J=3, 11 Hz, 1H), 4.95–5.10 (m, 1H), 7.30–7.65 (m, 4H), 7.70–7.80 (m, 1H), 7.93–8.05 (m, 1H); $^{13}$C NMR ($CDCl_3$, 75.469 MHz) δ 28.25, 32.08, 37.74, 38.90, 69.46, 78.66, 123.26, 125.63, 125.76, 126.30, 127.40, 129.01, 131.49, 134.00, 135.99; exact mass m/z calcd for $C_{16}H_{20}O_6S_2$ 372.0702, found 372.0694.

(c) 1-(3-Butenyl)naphthalene from dimesylate

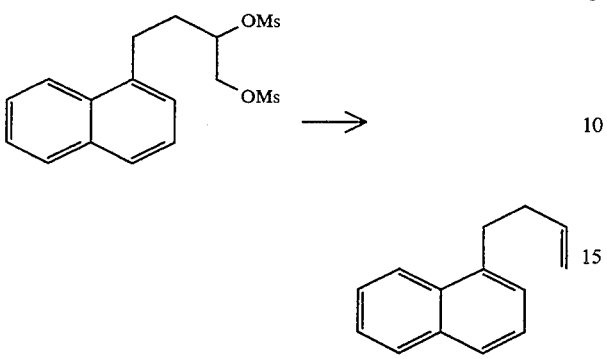

Tellurium powder (200 mesh, 0.1674 g, 1.311 mmol) and a small stirring bar were placed in a dry round-bottomed flask fused onto a reflux condenser. The flask was closed with a septum and flushed with argon. Super-Hydride (1M in THF, 3.4 mL, 3.4 mmol) was injected and the mixture was stirred until a milky white suspension had formed (ca. 5 h). 4-(1-Naphthyl)butane-1,2-diol dimethanesulfonate (488.3 mg, 1.311 mmol) in THF (5 mL) was then injected dropwise and the mixture was stirred for 20 h. The mixture was washed out of the flask with acetone and evaporated at room temperature. Flash chromatography of the residue over silica gel (2×30 cm) with hexane gave the pure (TLC, silica, hexane) olefin (0.2105 g, 88.1%). (Cf. J. B. Lambert et al.)

Example 3

Preparation of Oleic Acid Benzyl Ester (a) Benzyl (±)-(9S*,10R*)-9,10-dihydroxyoctadecanoate

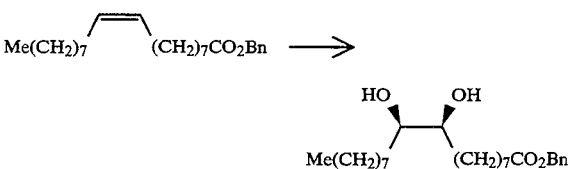

Osmium tetroxide (3.95 mL, 2.5% w/w solution of $OsO_4$ in t-BuOH) was added to a solution of oleic acid benzyl ester (see H. A. Shonle et al., J. Am. Chem. Soc. 1921, 43, 361) (5.6586 g, 15.1872 mmol) and 4-methyl-morpholine-N-oxide (3.749 g, 27.77 mmol) in acetone (500 mL) and water (38 mL). The mixture was stirred at room temperature for 24 h, and then evaporated at room temperature to ca. 100 mL. EtOAc (200 mL) was added, the organic layer was washed with water (1×200 mL) and 10% aqueous $Na_2SO_3$ (3×200 mL), dried ($MgSO_4$) and evaporated. Flash chromatography of the residue over silica gel (10×50 cm), using 3.2% MeOH in $CHCl_3$, gave the diol (4.4327 g, 72%): FTIR ($CHCl_3$, cast) 3280, 1735 cm$^{-1}$; $^1$H NMR ($CDCl_3$, 400 MHz) δ 0.80–1.00 (m, 3H), 1.20–1.58 (m, 24H), 1.58–1.75 (m, 2H), 1.95 (broad s, 2H), 2.35 (t, J=7.2, 2 H), 3.50–3.70 (m, 2H), 5.11 (s, 2H), 7.28–7.45 (m, 5H); $^{13}$C NMR ($CDCl_3$, 75.469 MHz) δ 14.13, 22.70, 24.93, 25.95, 26.06, 29.06, 29.18, 29.31, 29.46, 29.59, 29.73, 31.21, 31.91, 34.34, 66.12, 74.69, 74.76, 128.20, 128.58, 173.70; exact mass m/z calcd for $C_{25}H_{42}O_4$ 406.6015, $C_{25}H_{42}O_4-2H_2O$ 370.2873, found 370.2869. Chemical ionization mass m/z calcd for $[C_{25}H_{42}O_4+NH_4]^+$ 424, found 424.

(b) Benzyl (±)-(9S*10R*)-9,10-dihydroxyoctadecanoate dimethanesulfonate

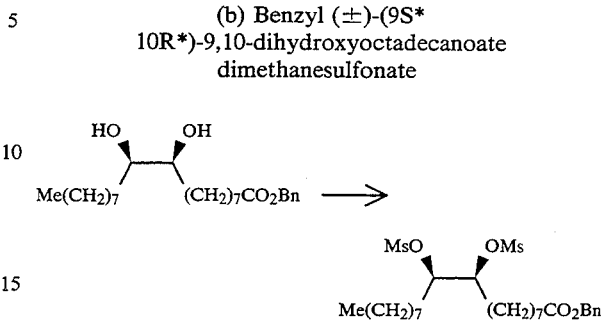

Methanesulfonyl chloride (1.8 mL, 23.02 mmol) in $CHCl_3$ (4 mL), was added dropwise to a stirred and cooled (0° C.) solution of benzyl (±)-(9S*,10R,)-9,10-dihydroxyoctadecanoate (1.1700 g, 2.878 mmol) and pyridine (3.80 ml, 46.04 mmol) in $CHCl_3$ (11 mL) (argon atmosphere). The ice bath was removed and stirring was continued for 40 h. The mixture was poured onto ice (ca. 50 g) and extracted with $CHCl_3$ (200 mL). The organic extract was washed with 10% aqueous $CuSO_4$ (2×100 mL) and aqueous NaOH (0.5 M, 1×50 mL), dried ($MgSO_4$) and evaporated. Flash chromatography of the residue over silica gel (3×30 cm), using 5% MeOH in $CHCl_3$, gave the dimesylate (1.5326 g, 95%), which contained a trace of impurity (signals at δ 3.0 and 3.1) but was suitable for the next stage: FT-IR ($CHCl_3$, cast) 1734, 1357, 1175 cm$^{-1}$; $^1$H NMR ($CDCl_3$, 200 MHz) δ 0.78–0.98 (m,3 H), 1.18–1.88 (m, 26 H), 2.35 (t, J=7 Hz, 2H), 3.09 (s, 6 H), 4.68–4.88 (m, 2H), 5.10 (s, 2H), 7.25–7.38 (m, 5H); $^{13}$C NMR ($CDCl_3$, 75.469 MHz) δ 14.07, 22.50, 22.61, 24.81, 25.36, 25.45, 28.91, 29.14, 29.27, 29.58, 29.65, 31.77, 34.22, 38.82, 66.06, 82.81, 82.91, 128.15, 128.54, 136.14, 173.52; exact mass m/z calcd for $C_{27}H_{46}O_8S_2$ 562. 2636, $C_{27}H_{46}O_8S_2+1H^+$ 563. 2714, found 563.2732.

(c) Oleic acid benzyl ester from dimesylate. Use of Te——

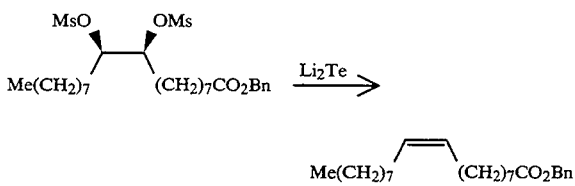

Tellurium powder (200 mesh, 52.8 mg, 0.412 mmol) and a small stirring bar were placed in a dry round-bottomed flask fused onto a reflux condenser. The flask was closed with a septum and flushed with argon. Super-Hydride (1M in THF, 0.78 mL, 0.78 mmol) was injected and the mixture was stirred until a milky white suspension had formed (ca. 5 h). The dimesylate (108.3 mg, 0.1924 mmol) in dioxane (5 mL) was then injected dropwise and the mixture was stirred for 14 h. Starting material (TLC, silica, 40:60 $CH_2Cl_2$-hexane) was still present and so the mixture was heated at 100° C. for 2 h (TLC control). The mixture was cooled, washed out of the flask with hexane, and evaporated at room temperature. Flash chromatography of the residue over silica gel (1.5×20 cm), using 40:60 CH$_2$Cl$_2$-hexane, gave the olefin (59.2 mg, 83%). (Cf. H. A. Shonle et al.).

(d) Oleic acid benzyl ester from dimesylate. Use of Se⁻⁻

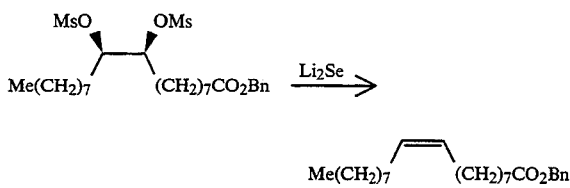

Selenium powder (325 mesh, 28.6 mg, 0.3593 mmol) and a small stirring bar were placed in a dry round-bottomed flask fused onto a reflux condenser. The flask was closed with a septum and flushed with argon. Super-Hydride (1M in THF, 0.68 mL, 0.68 mmol) was injected and the mixture was stirred until a milky white suspension had formed (ca. 20 min). The dimesylate (101.1 mg, 0.1796 mmol) in dioxane (5 mL) was then injected dropwise and the mixture was stirred for 24 h. Starting material was still present (TLC, silica gel, 40:60 CH$_2$Cl$_2$-hexane), and the mixture was therefore heated at 100° C. for 4 h. The mixture was cooled, washed out of the flask with hexane, and evaporated at room temperature. Flash chromatography of the residue over silica gel (1×30 cm), using 35:65 CH$_2$Cl$_2$-hexane, gave the olefin (50.8 mg, 76%).

Example 4

Preparation of methyl 5-O-Benzyl-2,3-dideoxy-β-D-pent-2-enofuranoside (a) Methyl 5-O-benzyl-2,3-Di-O-mesyl-β-D-ribofuranoside

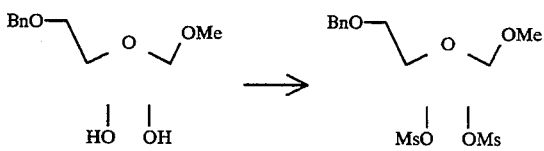

Methanesulfonyl chloride (1.58 mL, 20.49 mmol) in CH$_2$Cl$_2$ (10 mL), was added dropwise to a stirred and cooled (0° C.) solution of methyl 5-O-benzyl-β-D-ribofuranoside (See M. Kawana et al., Bull. Chem. Soc. Jpn., 1981, 54, 1492) (1.3025 g, 5.1223 mmol) and pyridine (3.31 mL, 40.98 mmol) in CH$_2$Cl$_2$ (10 mL) (argon atmosphere). The ice-bath was removed and stirring was continued for 24 h. The mixture was poured onto ice (ca. 50 g) and extracted with EtOAc (100 mL). The organic extract was washed with 10% aqueous CuSO$_4$ (2×50 mL), dried (MgSO$_4$), and evaporated. Flash chromatography of the residue over silica gel (3×30 cm), using 30:70 EtOAc-hexane, gave the dimesylate (1.9635 g, 93%): FTIR (CH$_2$Cl$_2$, cast) 1384, 1180 cm⁻¹; $^1$H NMR (CDCl$_3$, 300 MHz) δ 2.97 (s, 3H), 3.15 (s, 3H), 3.41 (s, 3H), 3.62 (dd, J=5.0, 10.5 Hz, 1H), 3.70 (dd, J=4.4, 10.5 Hz, 1H), 4.40 (add, J=4.5, 5.0, 6.5 Hz, 1H) 4.58 (q, J=12.0, 17.0 Hz, 2H), 4.98 (dd, J= 1.5, 5.0 Hz, 1H) 5.08 (d, J=1.5 Hz, 1H), 5.20 (dd, J=5.0, 6.5 Hz, 1H), 7.28-7.45 (m, 5H); $^{13}$C NMR (CDCl$_3$, 75.469 MHz) δ 38.12, 38.50, 55.65, 69.79, 73.74, 77.26, 79.15, 79.79, 105.68, 127.91, 128.02, 128.54, 137,49; exact mass m/z calcd for C$_{15}$H$_{22}$O$_9$S$_2$ 410.0706, found 410.0734.

(b) Methyl 5-O-benzyl-2,3-dideoxy-β-D-pent-2-enofuranoside

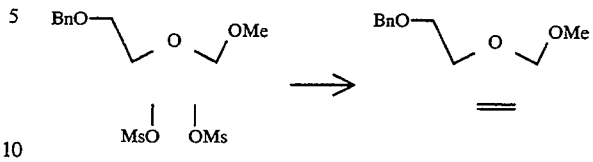

Tellurium powder (200 mesh, 72.1 mg, 0.565 mmol) and a small stirring bar were placed in a dry round-bottomed flask fused onto a reflux condenser. The flask was closed with a septum and flushed with argon. Super-Hydride (1M in THF, 1.27 ml, 1.27 mmol) was injected and the mixture was stirred until a milky white suspension had formed (ca. 5 h). Methyl 5-O-benzyl-2,3-di-O-mesyl-β-D-ribofuranoside (100.3 mg, 0.244 mmol) in dioxane (5 mL) was then injected dropwise and the mixture was refluxed for 20 h. At this stage all of the dimesylate had reacted (TLC, silica, 30:70 ethyl acetate-hexane). The mixture was cooled, washed out of the flask with acetone, and evaporated at room temperature. Flash chromatography of the residue over silica gel (1×20 cm), using 10% EtOAc in hexane, gave the olefin (37.3 mg, 69%). (Cf. M. Taniguchi et al., Tetrahedron 1974, 30, 3547 and K. Koga et al., Tetrahedron Lett. 1971, 263).

Example 5

Preparation of 2', 3'-Didehydro-2',3'-dideoxy-5'-O-(triphenylmethyl)uridine (a) 5'-O-(Triphenylmethyl)uridine

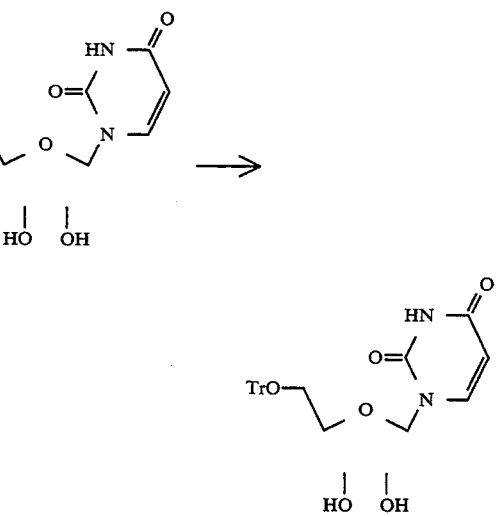

Uridine (155 mg, 0.6347 mmol), trityl chloride (199.4 mg, 0.7153 mmol), and a small stirring bar were placed in a dry round-bottomed flask fused onto a reflux condenser. The flask was closed with a septum and flushed with argon. Pyridine (1.90 mL) was injected and the mixture was stirred at room temperature for 48 h. The mixture was then heated for 0.5 h at 100° C. (oil bath temperature), cooled, and poured onto ice (ca. 25 g). The gummy product was filtered off, washed with water, and dissolved in acetone. Evaporation of the solvent and flash chromatography of the residue over silica gel (2×30 cm), using 5% MeOH in CH$_2$Cl$_2$ gave the pure (TLC) product (250.7 mg, 81%). (Cf. J. F.

Codington et al., J. Org. Chem. 1964, 29,558 and W. W. Zorbach et al. Ed. "Synthetic Procedures in Nucleic Acid Chemistry"; Wiley 1968, Vol I, p. 441).

(b) 5'-O-(Triphenylmethyl)uridine 2',3'-dimethanesulfonate

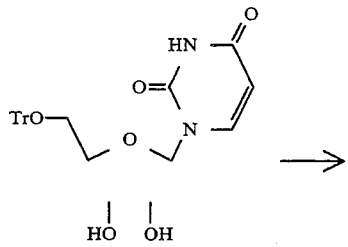

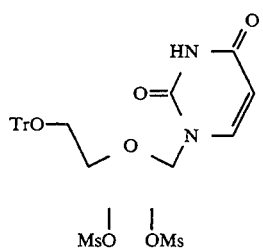

Methanesulfonyl chloride (1.45 mL, 18.76 mmol) in CH2Cl2 (8 mL) was added dropwise to a stirred and cooled (0° C.) solution of 5'-O-(triphenylmethyl)uridine (2.2816 g, 4.69 mmol) and pyridine (3.03 mL, 37.5 mmol) in CH2Cl2 (10 mL) (argon atmoshphere). The ice-bath was removed and stirring was continued for 48 h. The mixture was poured onto ice (ca. 100 g) and extracted with EtOAc (2×100 mL). The organic extract was washed with water (2×100 mL), aqueous NaOH (0.5M, 1×50 mL), and 10% aqueous CuSO4 (1×100 mL), dried (MgSO4) and evaporated. Flash chromatography of the residue over silica gel (4×30 cm), using 3% MeOH in CH2Cl2, gave the pure [$^1$H NMR (200 MHz)] dimesylate (2.6032 g, 86%): FTIR (CH2Cl2, cast) 1694, 1364, 1179 cm$^{-1}$;$^1$H NMR (CDCl3, 200 MHz) δ 3.10 (s, 3H), 3.21 (s, 3H), 3.50–3.75 (m, 2H), 4.25–4.50 (m, 1H), 5.25–5.65 (m, 3H) 6.02 (d, J=3 Hz, 1H), 7.10–7.60 (m, 15H), 7.72 (d, J=8 Hz, 1H), 9.32 (broad s, 1H); $^{13}$C NMR (CDCl3, 100 MHz) δ 38.62, 38.86, 60.87, 73.58, 78.24, 80.93, 88.18, 88.43, 103.20, 127.69, 128.24, 128.73, 139.95, 142.68, 150.49, 163.02; FABMS m/z calcd for [C30H30N2O10S2+H]+ 643.1412, found 643.1401.

(c) 2',3'-Didehydro-2',3'-dideoxy-5'-O-(triphenylmethyl)uridine

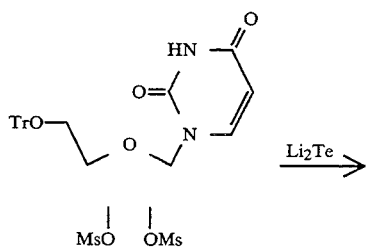

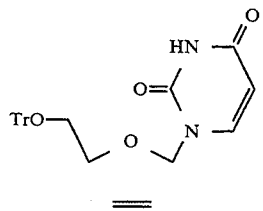

Tellurium powder (200 mesh, 40.0 mg, 0.3135 mmol) and a small stirring bar were placed in a dry round-bottomed flask fused onto a reflux condenser. The flask was closed with a septum and flushed with argon. Super-Hydride (1M in THF, 0.66 mL, 0.66 mmol) was injected and the mixture was stirred until a milky white suspension had formed (ca. 5 h). The dimesylate (100 mg, 0.1556 mmol) in dioxane (5 mL) was then injected dropwise and the mixture was stirred for 48 h. The mixture was washed out of the flask with CH2Cl2, and evaporated at room temperature. Flash chromatography of the residue over silica gel (2×25 cm), using 50:35:15 CH2Cl2-toluene-MeCN, gave the olefin (55.9 mg, 80%). (Cf. M. M. Masuri et al., J. Org. Chem. 1989, 54, 4780).

(d) 2',3'-Didehydro-2',3'-dideoxy-5'-O-(triphenylmethyl)uridine (i) Use of sodium selenide

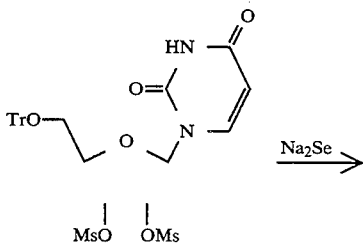

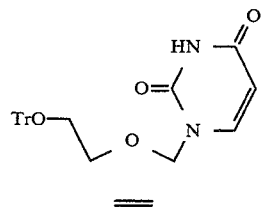

Na2Se (0.0302 g, 0.2417 mmol) (prepared from the elements, as described above) and a small stirring bar were placed in a dry round-bottomed flask fused onto a condenser. The flask was closed with a septum and flushed with argon. The dimesylate (595 mg, 0.0967 mmol) in THF (2 mL) was then injected and the mixture was stirred for 48 h. The mixture was washed out of the flask with CH2Cl2 and evaporated at room temperature. Flash chromatography of the residue over silica gel (1×25 cm), using 55:25:20 CH2Cl2-toluene-MeCN, gave, after a second chromatography under the same conditions, the olefin (21.3 mg, 51%).

(ii) Use of lithium selenide

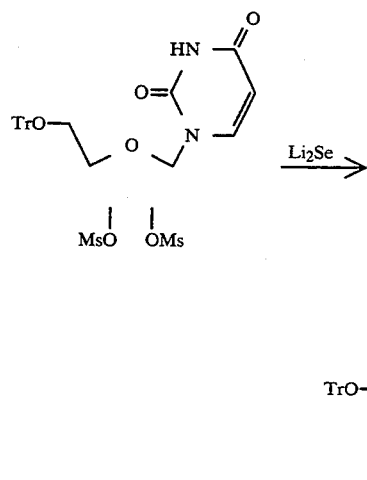

Selenium powder (325 mesh, 14.8 mg, 0.1867 mmol) and a small stirring bar were placed in a dry round-bottomed flask fused onto a reflux condenser. The flask was closed with a septum and flushed with argon. Super-Hydride (1M in THF, 0.37 mL, 0.37 mmol) was injected and the mixture was stirred for ca. 4 h. A milky white suspension was formed after 10 min. The dimesylate (59.0 mg, 0.0934 mmol) in THF (3 mL), was then injected dropwise and the mixture was stirred for 20 h. The mixture turned brown on initial addition of the dimesylate solution. The mixture was washed out of the flask with CH$_2$Cl$_2$, and K$_2$CO$_3$ was added. The mixture was then evaporated at room temperature. Flash chromatography of the residue over silica gel (1×20 cm), using 50:35:15 CH$_2$Cl$_2$-toluene-MeCN, gave the olefin (27.1 mg, 65%).

(iii) Use of sodium telluride

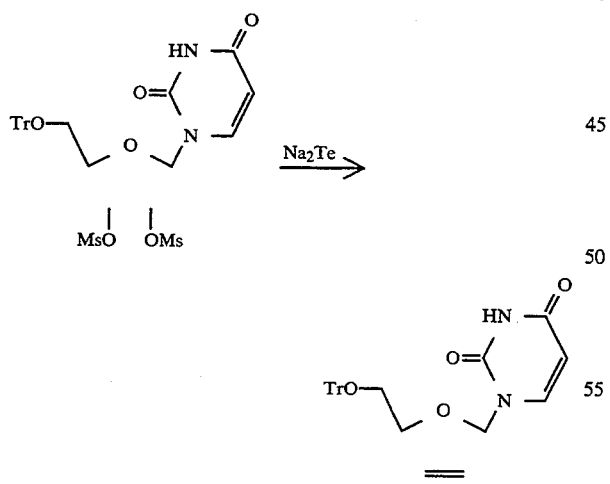

Na$_2$Te (0.0940 g, 0.5415 mmol) (prepared from the elements, as described above) and a small stirring bar were placed in a dry round-bottomed flask fused onto a condenser. The flask was closed with a septum and flushed with argon. The dimesylate (139.2 mg, 0.2166 mmol) in THF (2 mL) was then injected and the mixture was stirred for 20 h at room temperature. The mixture was washed out of the flask with CH$_2$Cl$_2$, and evaporated at room temperature. Flash chromatography of the residue over silica gel (1×25 cm), using 55:25:20 CH$_2$Cl$_2$-toluene-MeCN, gave the olefin (91.7 mg, 93%).

(iv) Use of lithium telluride in the presence of ethanol

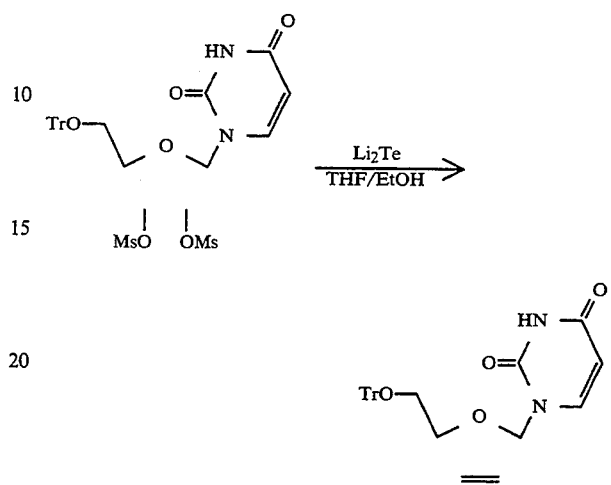

Telluride powder (200 mesh, 41.7 mg, 0.3268 mmol) and a small stirring bar were placed in a dry round-bottomed flask fused onto a reflux condenser. The flask was closed with a septum and flushed with argon. Super-Hydride (1M in THF, 0.73 mL, 0.73 mmol) was injected and the mixture stirred until a milky white suspension had formed (ca. 5 h). Ethanol (1 mL) was added. The dimesylate (100.0 mg, 0.1556 mmol) in ethanol (2 mL) was then injected dropwise and the mixture was stirred for 16 h. The reaction mixture was washed out of the flask with CH$_2$Cl$_2$ and evaporated at room temperature. Flash chromatography of the residue over silica gel (1×30 cm), using 55:25:20 CH$_2$Cl$_2$— toluene-MeCN, gave the olefin (26.5 mg, 38%).

(v) Use of lithium telluride in the presence of acetonitrile

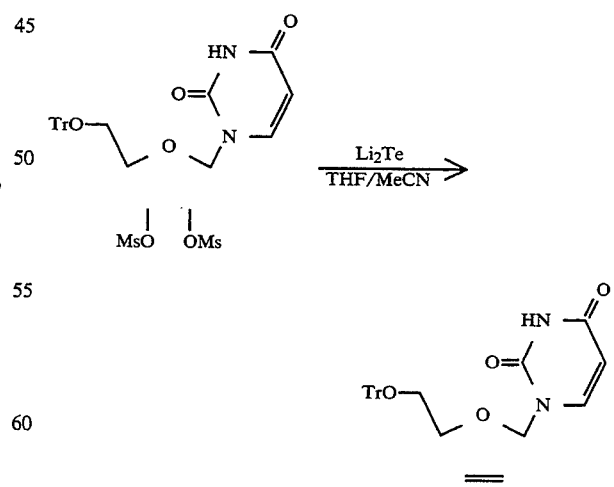

Tellurium powder (200 mesh, 41.7 mg, 0.3268 mmol) and a small sitrring bar were placed in a dry round-bottomed flask fused onto a reflux condenser. The flask was closed with a septum and flushed with argon. Super-Hydride (1M in THF, 0.73 mL, 0.73 mmol) was injected and the mixture stirred until a milky white suspension had formed (ca. 5 h). The dimesylate (100.0 mg, 0.1556 mmol) in acetonitrile (2 mL) was then injected dropwise and the mixture was stirred for 16 h. The reaction mixture was washed out of the flask with CH₂Cl₂ and evaporated at room temperature. Flash chromatography of the residue over silica gel (1×30 cm), using 55:25:20 CH₂Cl₂-toluene-MeCN, gave the olefin (70 mg, 99%).

Example 6

Preparation of 2',3'-Didehydro-2',3'-dideoxy-5-methyl-5'-O-(triphenylmethyl)uridine (a) 5-Methyl-5'-O-(triphenylmethyl)uridine

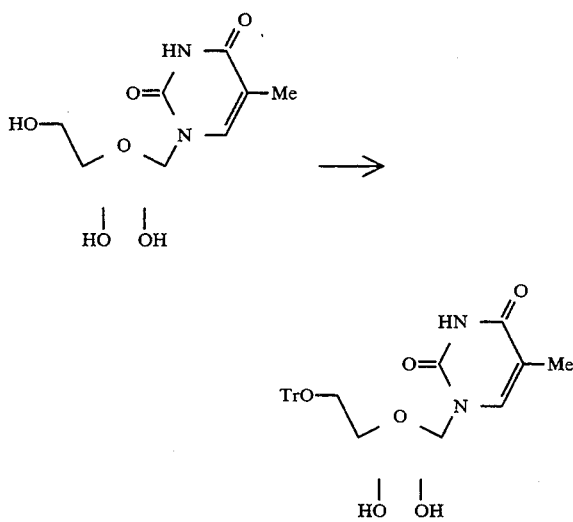

Ribothymidine (194.4 mg, 0.7529 mmol), trityl chloride (233.9 mg, 0.8390 mmol) and a small stirring bar were placed in a dry round-bottomed flask fused onto a reflux condenser. The flask was closed with a septum and flushed with argon. Pyridine (2.2 mL) was injected and the mixture was stirred at room temperature for 24 h. The mixture was poured onto ice (ca. 25 g) and the gummy product was filtered off, washed with water and dissolved in acetone. Evaporation of the solvent and flash chromatography of the residue over silica gel (2×25 cm), using 5% MeOH in CH₂Cl₂, gave the product (221.0 mg, 59%). (Cf. J. J. Fox et al., J. Am. Chem. Soc. 1957, 79, 2775).

(b) 5-Methyl-5'-O-(triphenylmethyl)uridine 2',3'-dimethansulfonate

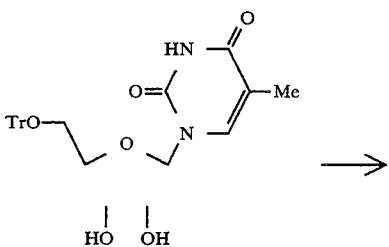

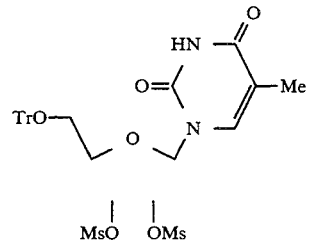

Methanesulfonyl chloride (0.11 mL, 1.391 mmol) in CH₂Cl₂ (1 mL) was added dropwise to a stirred and cooled (0° C.) solution of 5-methyl-5'-O-(triphenylmethyl)uridine (174.1 mg, 0.3478 mmol) and pyridine (0.46 mL, 5.6 mmol) in CH₂Cl₂ (3 mL) (argon atmosphere). The ice bath was removed and stirring was continued for 48 h. The mixture was poured onto ice (ca. 50 g) and extracted with EtOAc (2×50 mL). The organic extract was washed with water (2×50 mL), aqueous NaOH (0.1M, 1×50 mL), and 10% aqueous CuSO₄, dried (MgSO₄), and evaporated. Flash chromatography of the residue over silica gel (2×30 cm), using 3% MeOH in CH₂Cl₂, gave the pure [¹H NMR (200 MHz)] dimesylate (0.1898 g, 83%): FTIR (CH₂Cl₂, cast) 1693, 1364, 1180 cm⁻¹; ¹H NMR (CDCl₃,400 MHz) δ 1.42 (s, 3H), 3.08 (s, 3H), 3.20 (s, 3H), 3.48 (dd, J=2.2, 11.2 Hz, 1H), 3.64 (dd, J=2.2, 11.2 Hz, 1H), 4.30–4.45 (m, 1H), 5.40–5.55 (m, 2H), 6.08 (d, J=4.5 Hz, 1H), 7.20–7.60 (m, 16H), 9.69 (broad s, 1H); ¹³C NMR (CDCl₃, 50.323 MHz) δ 11.75 38.68, 38,84, 61.92, 74.96, 77.24, 81.48, 87.83, 88.23, 112.38, 127.71, 128.22, 128.77, 135.31, 142.92, 150.64, 163.39; FABMS m/z calcd for [C₃₁H₃₂N₂O₁₀S₂+H]+ 657.1578, found 657.1548.

(c)
2',3'-Didehydro-2',3'-dideoxy-5-methyl-5'-O-(triphenylmethyl)uridine

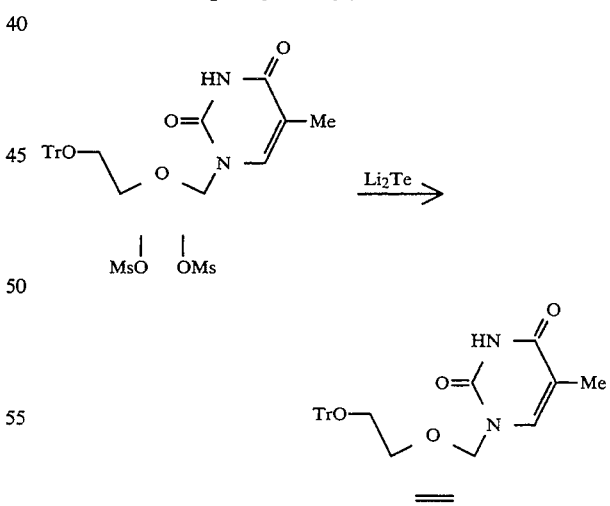

Tellurium powder (200 mesh, 24.9 mg, 0.1951 mmol) and a small stirring bar were placed in a dry round-bottomed flask fused onto a reflux condenser. The flask was closed with a septum and flushed with argon. Super-Hydride (1M in THF, 0.50 mL, 0.50 mmol) was injected and the mixture was stirred until a milky white suspension had formed (ca. 5 h). The dimesylate (60.1 mg, 0.0915 mmol) in THF (3 mL) was then injected dropwise and the mixture was stirred for 48 h. The mixture was washed out of the flask with CH₂Cl₂ and evaporated at room temperature. Flash chromatography of the residue over silica gel (2×30 cm), using 50:35:15 CH₂Cl₂-toluene-MeCN, gave the pure [¹H NMR (200 MHz)] olefin (38.6 mg, 90%). (Cf. N. D. P. Cosford et al., J. Org. Chem. 1991, 56, 2161).

Example 7

Preparation of 2',3'-Didehydro-2', 3'-dideoxy-5'-O-(triphenylmethyl)uridine (a) 5'-O-(Triphenylmethyl)uridine 2', 3'-di(p-toluenesulfonate)

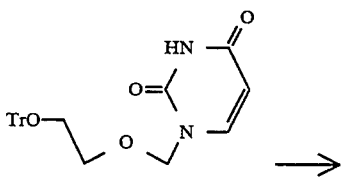

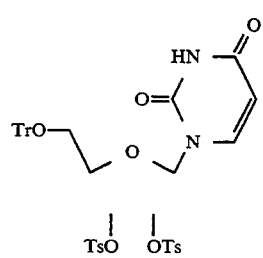

p-Toluenesulfonyl chloride (470 mg, 1.466 mmol) in CH₂Cl₂ (2 mL) was added dropwise to a stirred and cooled (0° C.) solution of 5'-O-(triphenylmethyl)uridine (200 mg, 0.4111 mmol), pyridine (0.80 mL, 9.9 mmol) and 4-(dimethylamino)pyridine (5 mg) in CH₂Cl₂ (2 mL) (argon atmosphere). The ice bath was removed, stirring was continued for 24 h and the mixture was then heated at 50° C. for a further 24 h. The mixture was poured onto ice (ca. 25 g) and extracted with CH₂Cl₂ (1×100 mL). The organic extract was washed with 10% aqueous CuSO₄ (2×50 mL), dried (MgSO₄) and evaporated. Flash chromatography of the residue over silica gel (1×30 cm), using 55:25:20 CH₂Cl₂-toluene-MeCN, gave the ditosylate (93.8 mg, 29%): ¹H NMR (CDCl₃,200 MHz) δ 2.40 (s, 3H), 2.45 (s, 3H), 3.30–3.50 (m, 2H), 4.30–4.45 (m, 1H), 5.00–5.35 (m, 3H), 6.10 (d, J=6 Hz, 1H), 7.15–7.45 (m, 20H), 7.64 (d, J=8 Hz, 2H), 7.77 (d, J=8 Hz, 2H), 7.96 (broad s, 1H).

(b) Conversion of 5'-O-(Triphenylmethyl)uridine 2', 3'-di(p-toluenesulfonate) into 2', 3'-Didehydro-2',3'-dideoxy-5'-O-(triphenylmethyl)uridine

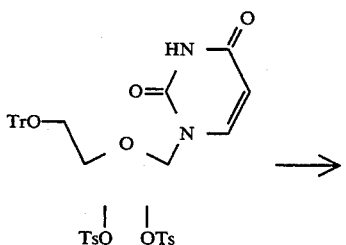

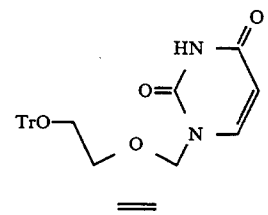

Tellurium powder (200 mesh, 11.7 mg, 0.0919 mmol) and a small stirring bar were placed in a dry round-bottomed flask fused onto a reflux condenser. The flask was closed with a septum and flushed with argon. Super-Hydride (1M in THF, 0.21 mL, 0.21 mmol) was injected and the mixture was stirred until a milky white suspension had formed (ca. 5 h). The ditosylate (34.8 mg, 0.0438 mmol) in THF (1 mL) was then injected dropwise and the mixture was stirred for 24 h. The mixture was washed out of the flask with CH₂Cl₂, and evaporated at room temperature. Flash chromatography of the residue over silica gel (1×30 cm), using 50:25:20 CH₂Cl₂-toluene-MeCN, gave the olefin (11.8 mg, 60%).

Example 8

Preparation of N-Acetyl-2', 3'-didehydro-2', 3'-dideoxy-5'-O-(triphenylmethyl)cytidine and N-Acetyl-(2', 3'-dideoxy-5'-O-(triphenylmethyl)cytidine (a) N-Acetyl-5'-O-(triphenylmethyl)cytidine

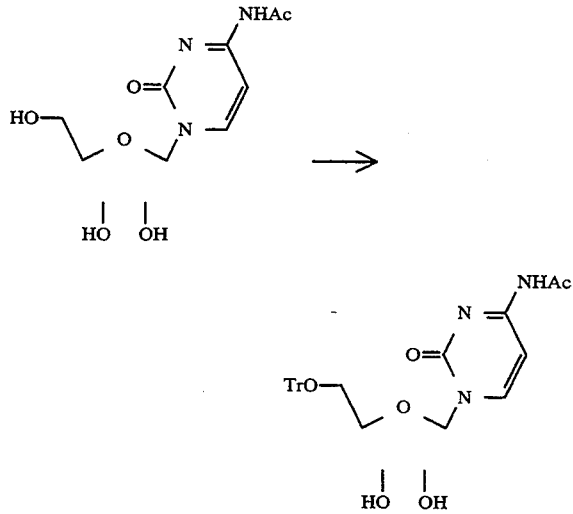

N-Acetylcytidine (see D. M. Brown et al., J. Chem. Soc. 1956, 2384) (1.000 g, 3.5057 mmol), trityl chloride (1.0751 g, 3.8563 mmol) and a small stirring bar were placed in a dry round-bottomed flask fused onto a reflux condenser. The flask was closed with a septum and flushed with argon. Pyridine (10.2 mL) was injected and the mixture was stirred at room temperature for 36 h. The mixture was evaporated, diluted with CH₂Cl₂, and again evaporated. The gummy residue was washed with water and the residue was dissolved in acetone. The solution was dried (MgSO₄) and evaporated. Flash chromatography of the residue over silica gel (4.5×30 cm), using 7% MeOH in CH₂Cl₂, gave the product (1.4752 g, 80%). (Cf. H. U. Blank et al., Justus Liebigs Ann. Chem. 1970, 742, 16).

(b) N-Acetyl-5'-O-(triphenylmethyl)cytidine 2',3'-dimethanesulfonate

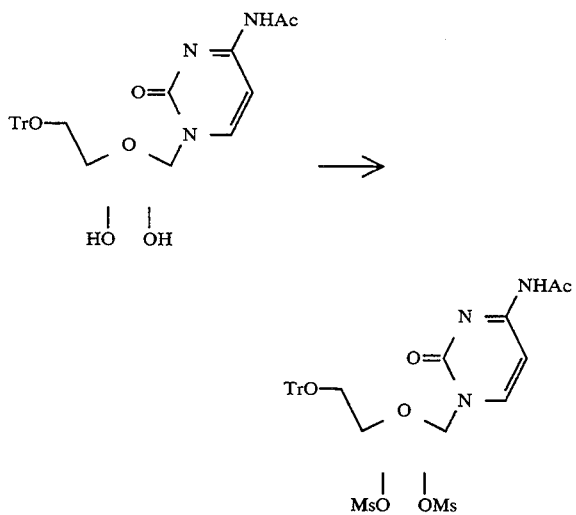

Methanesulfonyl chloride (0.0609 mL, 0.7862 mmol) in CH$_2$Cl$_2$ (0.6 mL) was added dropwise to a stirred and cooled (0° C.) solution of N-acetyl-5'-O-(triphenylmethyl)cytidine (0.1037 g, 0.1965 mmol) and triethylamine (0.0604 mL, 0.4339 mmol) in CH$_2$Cl$_2$ (1 mL) (argon atmosphere). The mixture was stirred at 0° C. for 25 min, poured onto ice (ca. 100 g), and extracted with CH$_2$Cl$_2$ (100 mL). The organic extract was washed with water (1×100 mL), saturated aqueous NaHCO$_3$ (1×100 mL), and water (1×100 mL), dried (MgSO$_4$) and evaporated. Flash chromatography of the residue over silica gel (1×30 cm), using 3.5% MeOH in CH$_2$Cl$_2$, gave the pure [$^1$H NMR (200 MHz)] dimesylate (0.1086 g, 81%): FTIR (CH$_2$Cl$_2$, cast) 1722, 1666, 1490, 1366, 1181 cm$^{-1}$; $^1$H NMR (CD$_2$Cl$_2$, 200 MHz) δ 2.18 (s, 3H), 3.06 (s, 3H), 3.35 (s, 3H), 3.56 (dd, J=2.2, 11.5 Hz, 1H), 3.68 (dd, J=2.2, 11.5 Hz, 1 H), 4.30–4.50 (m, 1H), 5.37–5.55 (m, 2H), 5.97 (s, br, 1H), 7.10 (d, J=7 Hz, 1H), 7.20–7.60 (m, 15 H), 8.25 (d, J=7 Hz, 1H), 8.90 (broad s, 1H); $^{13}$C NMR (CD$_2$Cl$_2$, 100.614 MHz) δ 25.01, 38.90, 39.24, 60.49, 72.58, 79.89, 80.58, 88.22, 90.44, 97.46, 127.87, 128.47, 128.65, 129.02, 143.12, 143.30, 144.85, 155.29, 163.71, 171.23; FABMS m/z calcd for [C$_{32}$H$_{33}$N$_3$O$_{10}$S$_2$+H]$^+$ 684.1687, found 684.1651.

(c) N-Acetyl-2', 3'-didehydro-2', 3'-dideoxy-5'-O-(triphenylmethyl)cytidine (i) Use of lithium telluride

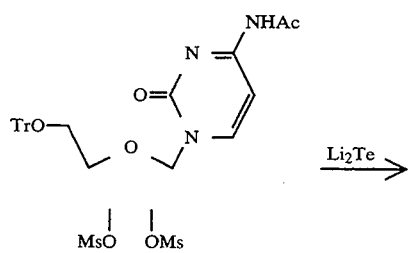

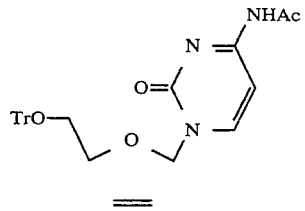

Tellurium powder (200 mesh, 39.2 mg, 0.3071 mmol) and a small stirring bar were placed in a dry round-bottomed flask fused onto a reflux condenser. The flask was closed with a septum and flushed with argon. Super-Hydride (1M in THF, 0.66 mL, 0.66 mmol) was injected and the mixture was stirred until a milky white suspension had formed (ca. 5 h). The dimesylate (100.0 mg, 0.1463 mmol) in THF (2 mL) was then injected dropwise and the mixture was stirred for 14 h. The mixture was washed out of the flask with CH$_2$Cl$_2$, and evaporated at room temperature. Flash chromatography of the residue over silica gel (1×15 cm), using 50:30:20 MeCN-CH$_2$Cl$_2$-toluene, gave the olefin (60.3 mg, 83%): $^1$H NMR (CD$_2$Cl$_2$, 200 MHz) δ 2.18 (s, 3H), 3.30–3.50 (m, 2H), 4.95–5.15 (m, 1H), 5.93–6.08 (m, 1H), 6.18–6.43 (m, 1H), 6.87 (d, J=7 Hz, 1H), 6.92–7.05 (m, 1H), 7.15–7.55 (m, 15H), 8.0 (d, J=7 Hz, 1H), 8.92 (broad s, 1H).

(ii) Use of sodium telluride

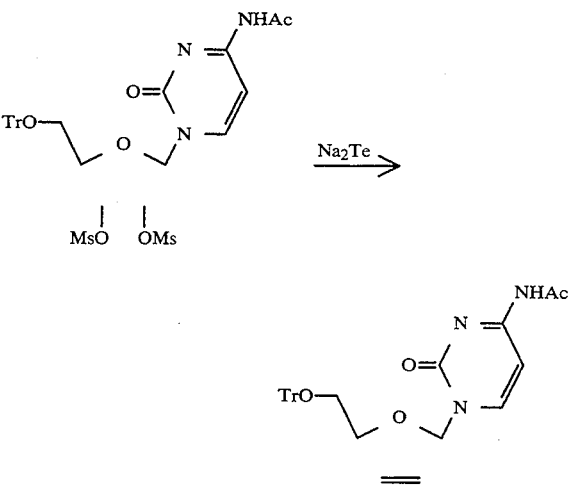

Na$_2$Te (0.0682 g, 0.3929 mmol) (prepared from the elements, as described above) and a small stirring bar were placed in a dry round-bottomed flask fused onto a condenser. The flask was closed with a septum and flushed with argon. The dimesylate (107.5 mg, 0.1572 mmol), in THF (2 mL) was then injected and the mixture was stirred for 24 h. The mixture was washed out of the flask with CH$_2$Cl$_2$, and evaporated at room temperature. Flash chromatography of the residue over silica gel (1×25 cm), using 50:30:20 MeCN-CH$_2$Cl$_{12}$-toluene, gave the olefin (33.0 mg, 42%).

(d) N-Acetyl-2',
3'-dideoxy-5'-O-(triphenylmethyl)cytidine by
Hydrogenation of
N-Acetyl-2',3'-didehydro-2',3'-dideoxy-5'-O-(triphenylmethyl)cytidine

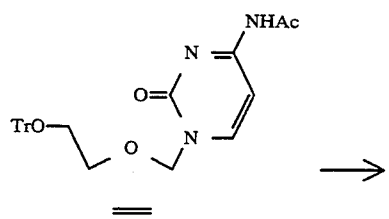

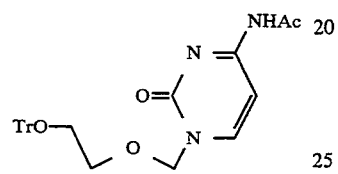

N-Acetyl-2',3'-didehydro-2',3'-dideoxy-5'-O-(triphenylmethyl)cytidine (0.498 g, 0.1009 mmol), EtOAc (3 mL) and MeOH (1 mL) were placed in a test tube along with Pd/charcoal (10%w/w, 10 mg). The test tube was supported with glass woold in a Parr vessel and shaken with hydrogen (50 psi) for 4 h. The mixture was filtered and evaporated. Flash chromatography of the residue over silica gel (1×30 cm), using 50:30:20 MeCN-CH₂Cl₂-toluene, gave the product (30.4 mg, 61%): ¹H NMR (CD₂Cl₂, 200 MHz) δ 1.82–2.03 (m, 1H), 2.20 (s, 3H), 2.35–2.63 (m, 1H), 3.28–3.58 (m, 2H), 4.17–4.38 (m, 1H), 5.95–6.10 (m, 1H), 7.12 (d, J=7 Hz, 2H), 7.20–7.60 (m, 15H), 8.32 (d, J=7 Hz, 2H), 9.68 (broad s, 1H).

Example 9

Preparation of 5-0-Acetyl-2'-3'-didehydro-2', 3'-dideoxyuridine (a) Preparation of 5'-O-Acetyluridine 2',3'-dimethanesulfonate (i) 2', 3'-O-Isopropylideneuridine

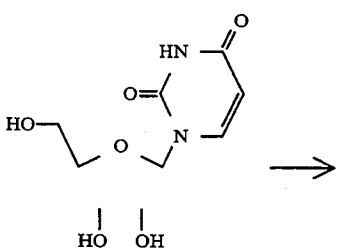

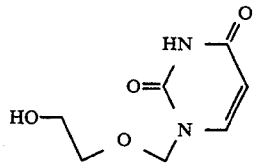

Uridine (1.000 g, 4.095 mmol), p-toluenesulfonic acid (101.3 mg, 0.5324 mmol), and a small stirring bar were placed in a dry round-bottomed flask fused onto a reflux condenser. The flask was closed with a septum and flushed with argon. Dry acetone (15 mL) and 2,2-dimethoxypropane (3.22 mL) were injected into the flask and the mixture was stirred at room temperature for 15 h. Sodium methoxide was then added until the solution became slightly basic (moist litmus paper). The mixture was evaporated at room temperature and flash chromatography of the residue over silica gel (3×30 cm), using 5% MeOH in CH₂Cl₂, gave the isopropylidene derivative (1.0587 g, 91%). (Cf. H. P. M. Fromageot et al., Tetrahedron 1967, 22, 2315).

(ii) 5'-O-Acetyluridine

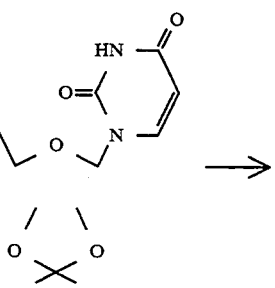

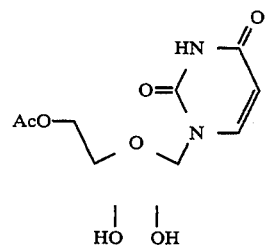

2', 3'-O-Isopropylideneuridine (130.2 rag, 0. 4580 mmol) and a small stirring bar were placed in a round-bottomed flask. The flask was sealed with a septum and flushed with argon. Pyridine (1 mL) and acetic anhydride (0.11 mL) were injected and the mixture was stirred at room temperature for 15 h. Methanol (0.37 mL) was added and the mixture was stirred for 1 h. The solution was evaporated three times from a 1:1 mixture of EtOH and water. The product was dissolved in formic acid (60%, 1.44 mL), and the solution was stirred for 3 h and then evaporated. Flash chromatography of the residue over silica gel (2×30 cm), using 7% MeOH in CH₂Cl₂, gave the product. (Cf. H. P. M. Fromageot et al.).

(iii) 5'-O-Acetyluridine 2',3'-dimethanesulfonate

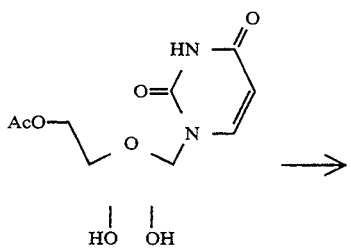

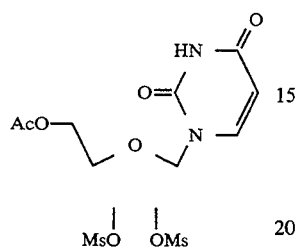

Methansulfonyl chloride (0.90 mL, 11.589 mmol), in CH₂Cl₂ (1.6 mL), was added dropwise to a stirred and cooled (ice bath) solution of 5'-O-acetyluridine (0.3317 g, 1.159 mmol) and pyridine (1.50 mL, 18.542 mmol) in CH₂Cl₂ (3 mL) (argon atmosphere). The ice bath was removed and stirring was continued for 24 h. The mixture was evaporated at room temperature, and flash chromatography of the residue over silica gel (3.5×30 cm), using 3% MeOH in CH₂Cl₂, gave, after a second chromatography under the same conditions, the pure [$^1$H NMR (200 MHz)] dimesylate (0.4177 g, 81%)]FTIR (MeOH, cast) 1365, 1180 cm$^{-1}$; $^1$H NMR (acetone-d$_6$, 200 MHz) δ 2.07 (s, 3H), 3.26 (s, 3H), 3.32 (s, 3H), 4.30–4.60 (m, 3H), 5.48 (t, J=6 Hz, 1H), 5.55–5.80 (m, 2H), 6.0 (d, J=3 Hz, 1H), 7.76 (d, J=8 Hz, 1H), 10.23 (broad s, 1H); $^{13}$C NMR (acetone-d$_6$, 50 MHz) δ 20.61, 38.66, 38.74, 62.58, 75.14, 78.61, 80.24, 91.11, 103.34, 141.93, 151.33, 163.36, 170.57; FABMS m/z calcd for [C$_{13}$H$_{18}$N$_2$O$_{11}$S$_2$+H]+ 443.0431, found 443.0398.

(b) 5'-O-Acetyl-2',3'-didehydro-2',3'-dideoxyuridine

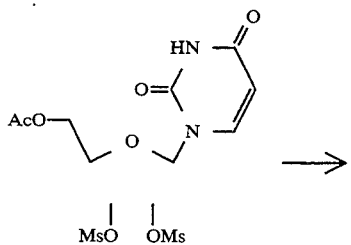

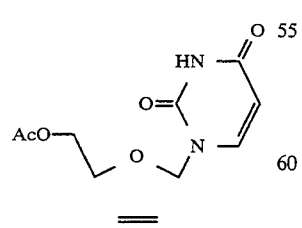

Tellurium powder (200 mesh, 60.6 mg, 0.4747 mmol) and a small stirring bar were placed in a dry round-bottomed flask, fused onto reflux condenser. The flask was closed with a septum and flushed with argon. Super-Hydride (1M in THF, 1.17 mL, 1.17 mmol) was injected and the mixture was stirred until a milky white suspension had formed (ca. 5 h). The dimesylate (100.0 mg, 0.2260 mmol) in THF (3 mL) was then injected dropwise and the mixture was stirred for 96 h. The mixture was washed out of the flask with CH₂Cl₂ and evaporated at room temperature. Flash chromatography of the residue over silica gel (1×30 cm), using 3% MeOH in CH₂Cl₂, gave the olefin (7.7 mg, 14%). (Cf. Y. Amino et al., Chem. Pharm. Bull. 1991, 39, 622).

Example 10

Preparation of 2', 3'-Didehydro-2', 3'-dideoxy-N[(dimethylamino)methylene]-5'-O-[bis (4-methoxyphenyl) phenylmethyl]adenosine (a)
N-[(Dimethylamino)methylene]-5'-O-[bis(4-methoxyphenyl)phenylmethyl]adenosine 2', 3'-dimethanesulfonate

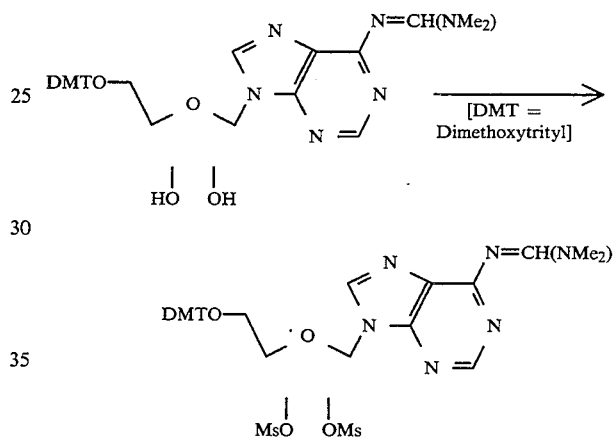

Methanesulfonyl chloride (0.37 mL, 4.8073 mmol) in CH₂Cl₂ (5 mL) was added dropwise to a stirred and cooled (0° C.) solution of N-[(dimethylamino)methylene]-5'-O-[bis(4-methoxyphenyl)phenylmethyl]adenosine (see R. Vinayak et al., Nucleic Acids Research, 1992, 20, 1265) (1.001 g, 1.6024 mmol) and triethylamine (1.34 mL, 9.6145 mmol) in CH₂Cl₂ (8 mL) (argon atmoshphere). The mixture was stirred at 0° C. for 30 min, poured onto ice (ca. 200 g), and extracted with CH₂Cl₂ (2×150 mL). The organic extract was washed with water (1×100 mL), saturated aqueous NaHCO₃ (1×100 mL), and water (1×100 mL), dried (MgSO₄) and evaporated. Flash chromatography of the residue over silica gel (3×30 cm), using 49:30:20:1CH₂Cl₂-toluene-MeCN-Et₃N, gave the pure [$^1$H NMR (200 MHz)] dimesylate (1.0895 g, 87%). FTIR (CH₂Cl₂, cast) 1365, 1180 cm$^{-1}$; $^1$H NMR (acetone-d$_6$, 200 MHz) δ 3.10–3.30 (m, 12 H), 3.40 (dd, J=4, 11 Hz, 1H), 3.62 (dd, J=3.5, 11 Hz, 1H), 3.75 (s, 3H), 3.76 (s, 3H), 4.40–4.60 (m, 1 H), 5.85–6.00 (m, 1H), 6.30–6.55 (m, 2H), 6.70–6.90 (m, 4H), 7.10–7.38 (m, 7H), 7.38–7.55 (m, 2H), 8.30 (s, 1H), 8.31 (s, 1H), 8.85–9.00 (s, br, 1H); $^{13}$C NMR (acetone-d$_6$, 50 MHz) δ 35.02, 38.74, 38.80, 41.13, 55.60, 62.99, 77.08, 77.47, 82.51, 87.67, 114.06, 127.68, 128,63, 129.14, 131.04, 136.53, 136.65, 145.76, 152.45, 153.25, 159.14, 159.82, 161.16; FABMS m/z calcd for C$_{36}$H$_{40}$N$_6$O$_{10}$S$_2$+H]+ 781.2328, found, 781.2337.

(b) 2',3'-Didehydro-2', 3'-dideoxy-N-[(dimethylamino)methylene]-5'-O-[bis(4-methoxyphenyl)phenylmethyl]adenosine

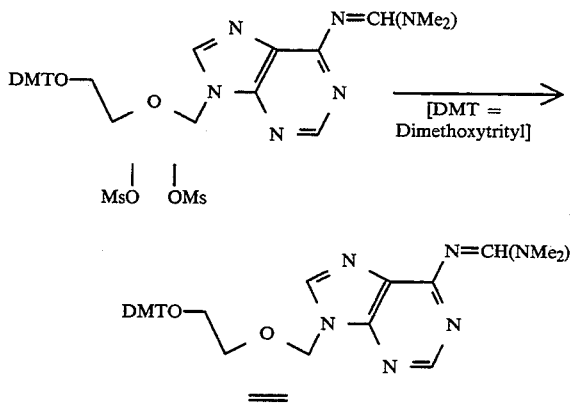

Tellurium powder (200 mesh, 19.9 mg, 0.156 mmol) and a small stirring bar were placed in a dry round-bottomed flask fused onto a reflux condenser. The flask was closed with a septum and flushed with argon. Super-Hydride (1M in THF, 0.33 mL, 0.33 mmol) was injected and the mixture was stirred until a milky white suspension had formed (ca. 5 h). The dimesylate (58 mg, 0.0742 mmol) in THF (2 mL) was then injected dropwise and the mixture was stirred for 16 h. The mixture was washed out of the flask with $CH_2Cl_2$, and evaporated at room temperature. Flash chromatography of the residue over silica gel (1×30 cm), using 29:20:50:1 $CH_2Cl_2$-toluene-MeCN-$Et_3N$, gave the olefin (39.1 mg, ca.89%), containing [$^1$H NMR (200 MHz)] trace impurities. 1H NMR (acetone-$d_6$, 200 MHz) δ 3.02–3.30 (m, 6H), 3.30–3.46 (m, 1H), 3.46–3.65 (m, 1H), 3.74 (s, 3H), 3.75 (s, 3H), 5.02–5.18 (m, 1H), 6.15–6.30 (m, 1H), 6.48–6.60 (m, 1H), 6.60–6.90 (m, 4H), 7.00–7.32 (m, 7H), 7.32–7.50 (m, 2H), 8.01 (s, 1H), 8.42 (s, 1H), 8.86–9.05 (s, 1H).

The terms and expressions used in this specification are used as terms of description and not of limitation. There is no intention, in using such terms and expressions, of excluding equivalents of the features shown and described, it being recognized that the scope of the invention is defined and limited only by the claims which follow. All publications referred to in the specification are incorporated herein by reference.

We claim:

1. A method of deoxygenating a cis vicinal diol compound to an olefin, comprising:
   (a) converting the vicinal diol groups into good leaving groups for nucleophilic substitution, said leaving groups leaving the hydroxy oxygen intact; and
   (b) reacting the product of (a) with a source of $Te^{2-}$ or $Se^{2-}$ ions to produce an olefin.

2. The method of claim 1, wherein step (a) comprises converting the diol groups to alkyl or aryl sulfonate groups.

3. The method of claim 2, wherein, the diol groups are converted to mesylate or tosylate groups.

4. The method of claim 1, wherein the $Te^{2-}$ or $Se^{2-}$ ions are provided as alkali or alkaline earth metal tellurides or selenides.

5. The method of claim 1, wherein the $Te^{2-}$ or $Se^{2-}$ ions are provided as alkali metal tellurides or selenides.

6. The method of claim 1, wherein the $Te^{2-}$ or $Se^{2-}$ ions are provided as lithium or sodium tellurides or selenides.

7. The method of claim 1, wherein step (b) is performed in an ethereal or alcoholic solvent or in acetonitrile.

8. The method of claim 1, wherein the cis vicinal diol is a carbohydrate.

9. The method of claim 1, wherein the diol is at the 2',3'-position in the sugar moiety of a nucleoside.

10. The method of claim 9, wherein the diol is O- and/or N- protected, except for the hydroxyl groups at the 2' and 3' positions.

11. The method of claim 10, wherein step (a) comprises converting the diol groups to alkyl or aryl sulfonate groups.

12. The method of claim 10, wherein, the diol groups are converted to mesylate or tosylate groups.

13. The method of claim 11, wherein the $Te^{2-}$ or $Se^{2-}$ ions are provided as alkali or alkaline earth metal tellurides or selenides.

14. The method of claim 11, wherein the $Te^{2-}$ or $Se^{2-}$ ions are provided as alkali metal tellurides or selenides.

15. The method of claim 12, wherein the $Te^{2-}$ or $Se^{2-}$ ions are provided as lithium or sodium tellurides or selenides.

16. The method of claim 14, wherein step (b) is performed in an ethereal or alcoholic solvent or in acetonitrile.

17. The method of claim 16, wherein the diol is a 5-methyl-5'-O-protected uridine.

18. The method of claim 16, wherein the diol is 5-methyl-5'-O-(triphenylmethyl)uridine.

19. The method of claim 16, wherein the diol is an N-protected-5'-O-protected cytidine.

20. The method of claim 16, wherein the diol is N-acetyl-5'-O-(triphenylmethyl)cytidine.

21. The method of claim 16, wherein the diol is a 5'-O-protected uridine.

22. The method of claim 16, wherein the diol is (triphenylmethyl)uridine.

23. The method of claim 16, wherein the diol is acetyluridine.

24. The method of claim 16, wherein the diol is an N-protected-5'-O-protected adenosine.

25. The method of claim 16, wherein the diol is N-(dimethyamino)methylene]-5'-O-[bis(4-methoxyphenyl)-phenylmethyl]adenosine.

26. The method of claim 8, wherein the diol is a methyl 5-O-protected-β-D-ribofuranoside.

27. The method of claim 26, wherein the diol is methyl 5-O-benzyl-β-D-ribofuranoside.

28. 5'-O-Protected uridine 2', 3'-dimethanesulfonate;
5'-O-(triphenylmethyl)Uridine 2', 3'-dimethanesulfonate;
5'-O-acetyluridine 2',3'-dimethanesulfonate;
5-methyl-5'-O-protected uridine 2',3'-dimethanesulfonate;
5-methyl-5'-O-(triphenylmethyl)uridine 2',3'-dimethanesulfonate;
5'-O-protected uridine 2',3'-di(p-toluene-sulfonate;
5'-O-(triphenylmethyl)uridine 2',3'-di(p-toluenesulfonate);
N-protected-5'-O-protected cytidine 2',3'-dimethanesulfonate;
N-acetyl-5'-O-(triphenylmethyl)cytidine 2',3'-dimethanesulfonate;

N-acetyl-2',3'-didehydro-2',3'-dideoxy-5'-0-(triphenylmethyl)cytidine;
N-acetyl-2',3'-dideoxy-5'-0-(triphenylmethyl)-cytidine;
N-protected-5'-0-protected adenosine 2',3'-dimethanesulfonate;
N-[dimethylamino) methylene-5'-O-[bis(4-methoxyphenyl)phenylmethyl]adenosine 2,',3'-dimethanesulfonate; or
2',3'-didehydro-2',3'-dideoxy-N-[(dimethyl-amino)-methylene]-5'-0-[bis(4-methoxyphenyl)phenylmethyl]-adenosine.

* * * * *

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Title Page: Item [54] Title of Invention, line 3: Change "NUCLEOSIDIES" to read -- NUCLEOSIDES --.

Under Example 4; column 9, line 36: After 2,3- Change "D;"to -- d;-- .

Under Example 4; column 9, lines 40-45: The formula should appear as follows:

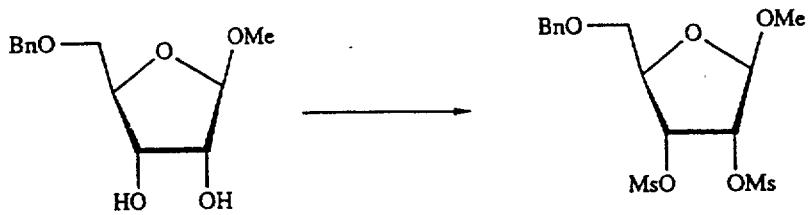

Under Example 4; column 9, line 62: Reads "(adds, J=4.5, 5.0, 6.5 Hz, 1H)" should read ... --(ddds, J=4.5, 5.0, 6.5 Hz,1 H), -- .

Under Example 4; column 10, lines 5-10: The formula should appear as follows:

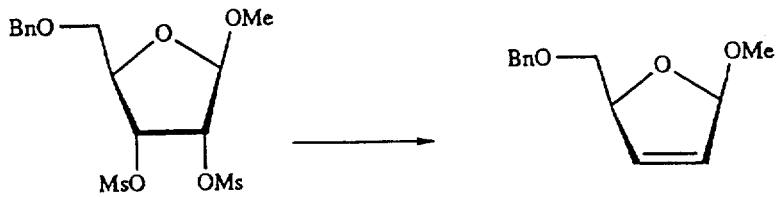

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 5; column 10, lines 35-55: The formula should appear as follows:

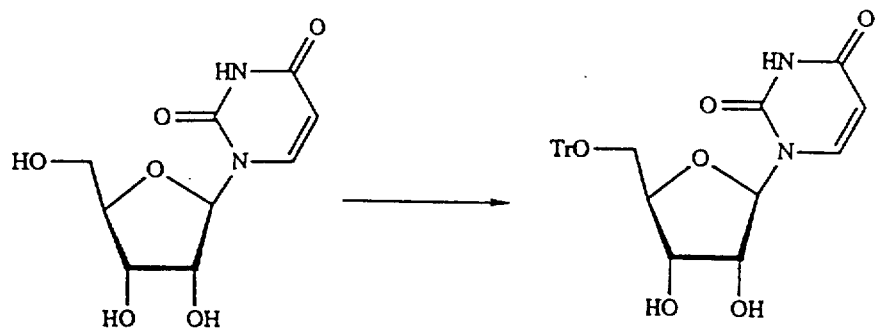

Under Example 5; column 11, line 1: Change "29,558" to -- 29, 558 --.

Under Example 5; column 11, lines 6-28: The formula should appear as follows:

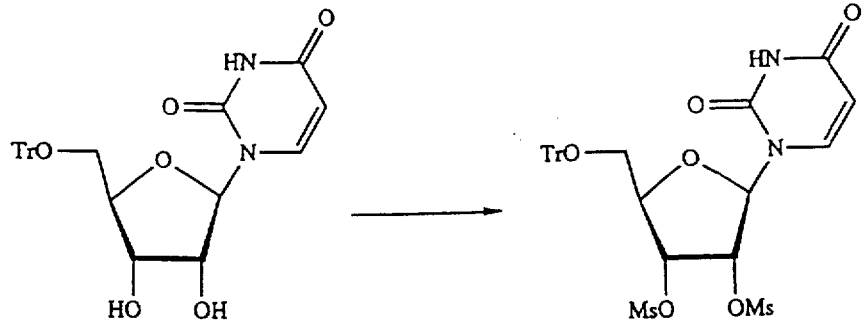

Under Example 5; column 11, line 47: Change "(m,15H)," to -- (m, 15 H), --.

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 5; column 11, line 47: Change "(d,J=8 Hz, 1H)," to -- (d, J=8 Hz, 1 H), --.

Under Example 5; column 11, line 54: Move "c" to line 55.

Under Example 5; column 11, line 55: After "(triphenylmethyl" delete "-" and replace with -- ) --.

Under Example 5; column 11, lines 59-67: The formula should appear as follows:

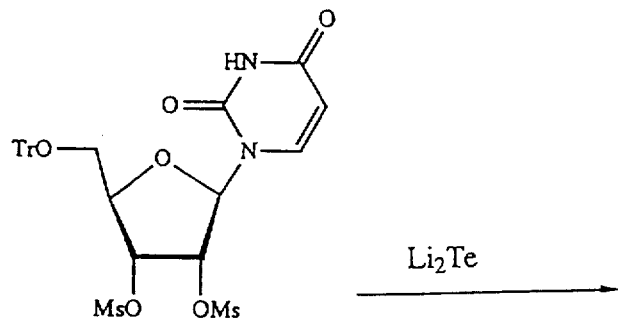

UNITED STATES PATENT AND TRADEMARK OFFICE
CERTIFICATE OF CORRECTION

PATENT NO. : 5,410,033
DATED : April 25, 1995      Page 4 of 23
INVENTOR(S) : Derrick L.J. CLIVE et al.

It is certified that error appears in the above-indentified patent and that said Letters Patent is hereby corrected as shown below:

Under Example 5; column 12, lines 1-10: The formula should appear as follows:

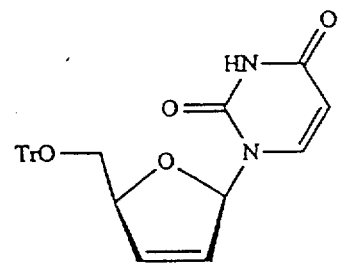

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 5; column 12, lines 35-54: The formula should appear as follows:

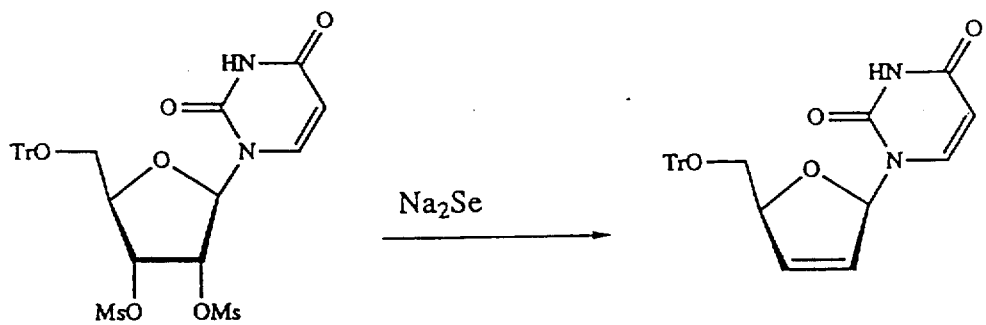

Under Example 5; column 13, lines 4-20: The formula should appear as follows:

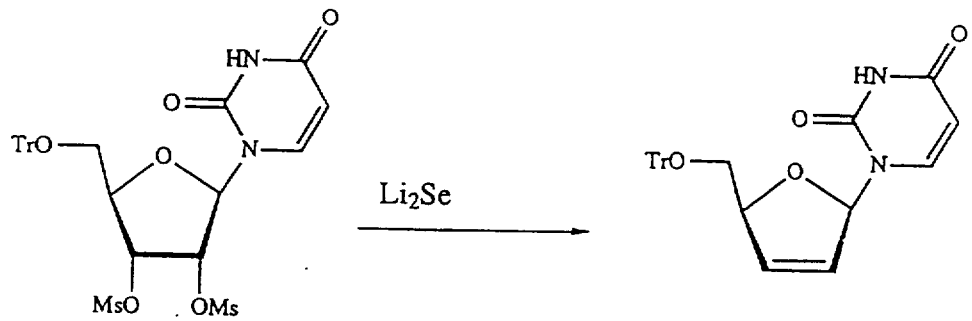

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 5; column 13, lines 40-58: The formula should appear as follows:

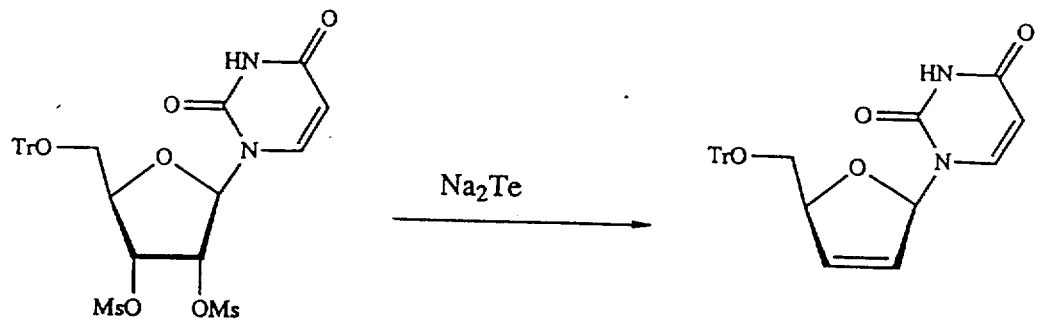

Under Example 5; column 14, lines 6-25: The formula should appear as follows:

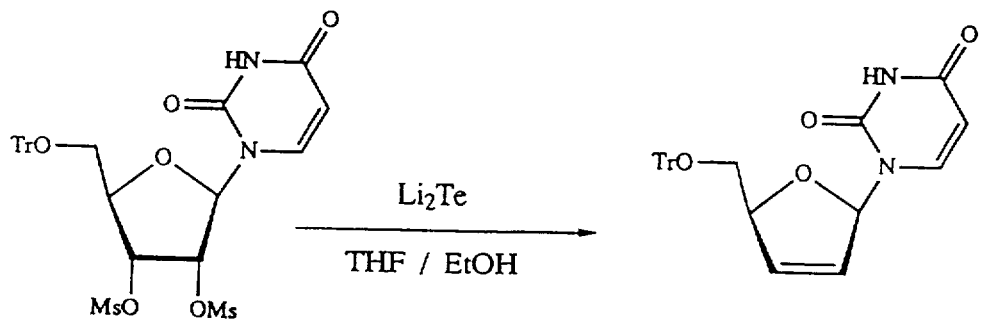

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 5; column 14, lines 45-63: The formula should appear as follows:

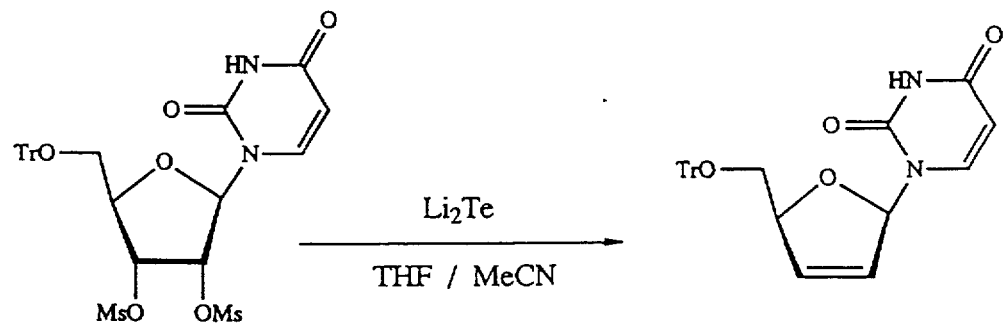

Under Example 6; column 15, lines 18-38: The formula should appear as follows:

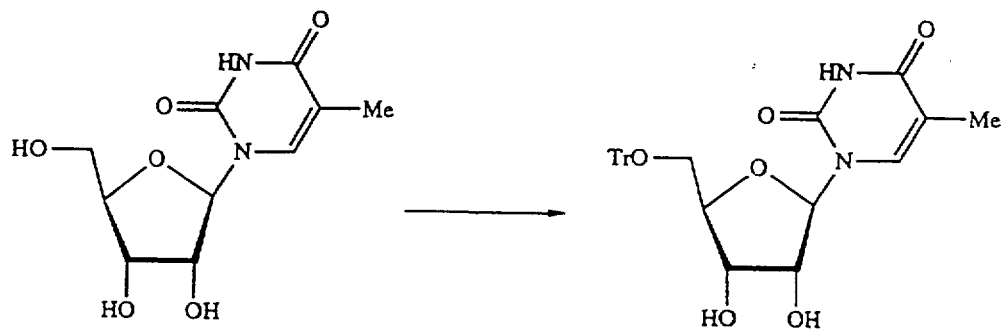

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 6; column 15 lines 59-67 and column 16, lines 3-12: the formula should appear as follows:

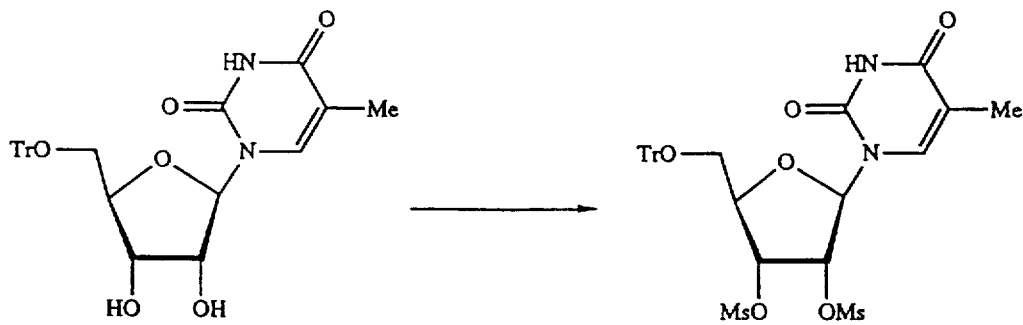

Under Example 6; column 16, line 27: Change "(s, 3H)" to read -- (s, 3 H) -- .

Under Example 6; column 16, line 28: Change "(s,3H)" to -- (s, 3 H) -- in both occurences.

Under Example 6; column 16, line 28: After Hz, change "1H" to -- 1 H -- .

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 6; column 16, line 29: After Hz change "1H" to -- 1 H --.

Under Example 6; column 16, line 29: Change "(m, 1H)" to read -- (m, 1 H) --.

Under Example 6; column 16, line 30: Change "(m, 2H)" to -- (m, 2 H) --.

Under Example 6; column 16, line 30: After Hz change "1H" to -- 1 H --.

Under Example 6; column 16, line 31: Change "16H" to -- 16 H --.

Under Example 6; column 16, line 31: Change "(broad, s 1H);" to -- (broad, s 1 H); --.

Under Example 6; column 16, line 32: Change "38,84 ," to -- 38.84, --.

Under Example 6; column 16, line 37: Move "c" to line 38.

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 6; column 16, lines 40-59: The formula should appear as follows:

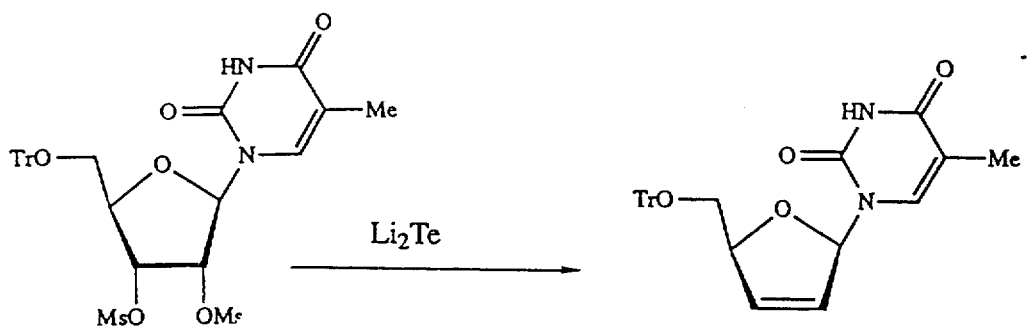

Under Example 7; column 17, lines 11-33: The formula should appear as follows:

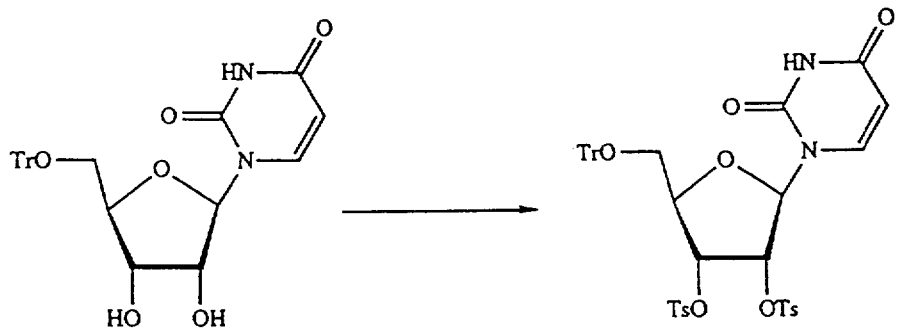

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 7; column 17, line 49: Change "(CDCl$_3$,200 MHz)" to -- (CDCl$_3$, 200 MHz) --.

Column 17, line 49: Change "(s,3H)" in both occurences to -- (s, 3 H) --.

Column 17, line 50: Change "(m, 2H)" to read -- (m, 2 H) --.

Column 17, line 50: Change "(m, 1H)" to read -- (m, 1 H) --.

Column 17, line 50: Change "(m, 3H)" to read -- (m, 3 H) --.

Column 17, line 51: After Hz change "1H" to -- 1 H --.

Column 17, line 51: Change "(m, 20H)" to -- (m, 20 H) --.

Column 17, line 51: After Hz, change "2H" to -- 2 H --.

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 7; column 17, line 53: After Hz change "2H" to - - 2 H - -.

Column 17, line 53: Change "1H" to - - 1 H - -.

Under Example 7; column 17, lines 58-68 and column 18, lines 4-11: The formula should appear as follows:

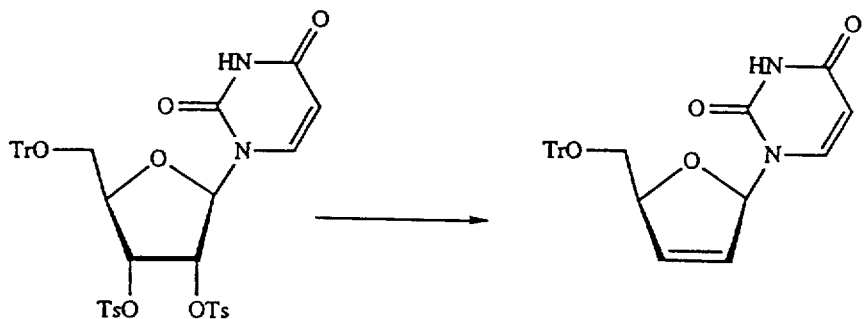

Under Example 7; column 18, line 16: Change "1M" to - - 1 M - -.

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 8; column 18, lines 35-54: The formula should appear as follows:

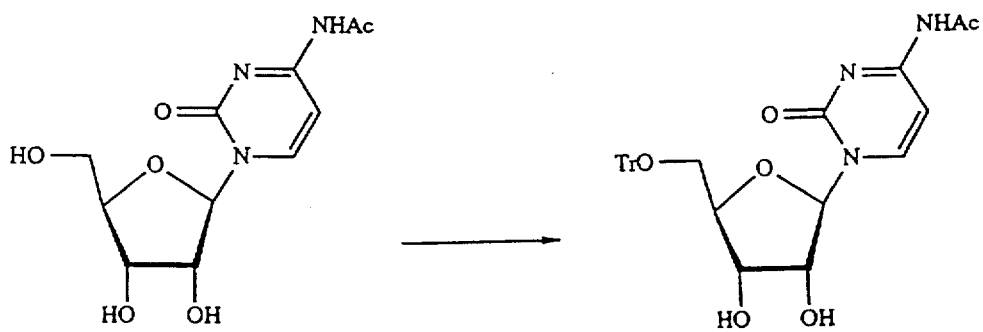

Under Example 8, column 19, lines 6-29: the formula should appear as follows:

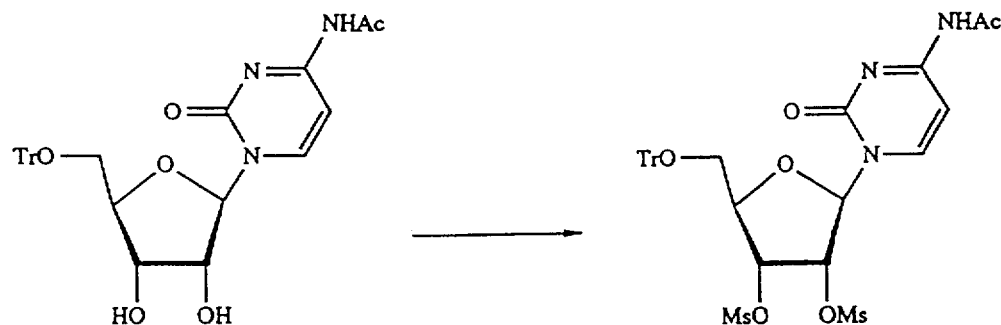

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 8; column 19, line 43: Change "(s,3H)" in all three occurences to -- (s, 3H) --.

Under Example 8, column 19, line 44: After Hz change "1H" to -- 1 H --.

Under Example 8, column 19, line 45: Change "(m,1H)" to -- (m, 1 H) --.

Column 19, line 45: Change "(m, 2H)" to -- (m, 2 H) --.

Column 19, line 45: Change "(s,br,1H)" to -- (s, br, 1 H) --.

Column 19, line 46: Change "1H" in both occurences to -- 1 H --.

Column 19, line 47: Change "(broad s, 1H)" to read -- (broad s, 1 H) --.

Under Example 8; column 19, lines 59-67 and column 20 lines 4-10: The formula should appear as:

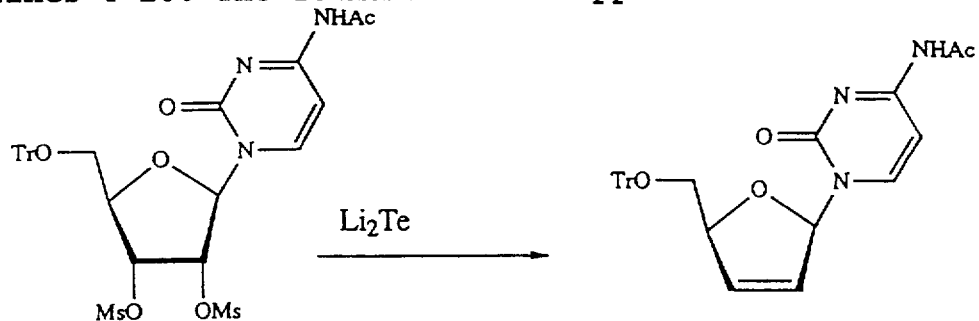

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 8; column 20, line 27: Change "3H" to -- 3 H --.

Column 20, line 28: Change "2H" to -- 2 H --.

Column 20, line 28: Change "1H" in both occurences to -- 1 H --.

Column 20, line 29: Change "1H" in both occcurences to -- 1 H --.

Column 20, line 30: Change "1H" in both occurences to --1 H --.

Column 20, line 30: Change "15H" to -- 15 H --.

Column 20, line 31: Change "1H" to -- 1 H --.

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 8; column 20, lines 36-54: The formula should appear as follows:

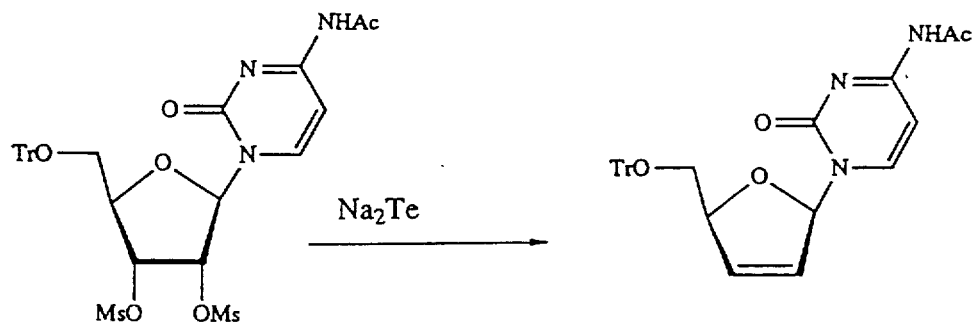

Under Example 8, column 21, lines 10-28: The formula should appear as follows:

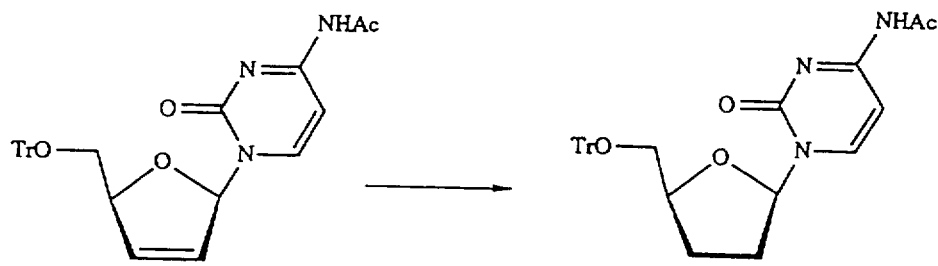

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 8; column 21, line 41: Change "1H" to - - 1 H - -.

Column 21, line 42: Change "3H" to read - - 3 H - -.
Column 21, line 42: Change "1H" to read - - 1 H - -.
Column 21, line 42: Change "2H" to read - - 2 H - -.

Under Example 8; column 21, line 43: Change "1H" in both occurences to - - 1 H - -.
Column 21, line 43: Change "2H" to - - 2 H - -.

Under Example 8;, column 21, line 44: Change "15H" to - -15 H - -.
Column 21, line 44: Change "2H" to - - 2 H - -.
Column 21, line 44: Change "1H" to - - 1 H - -.

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 9; column 21, lines 59-67 and column 22, lines 4-13: The formula should appear as follows:

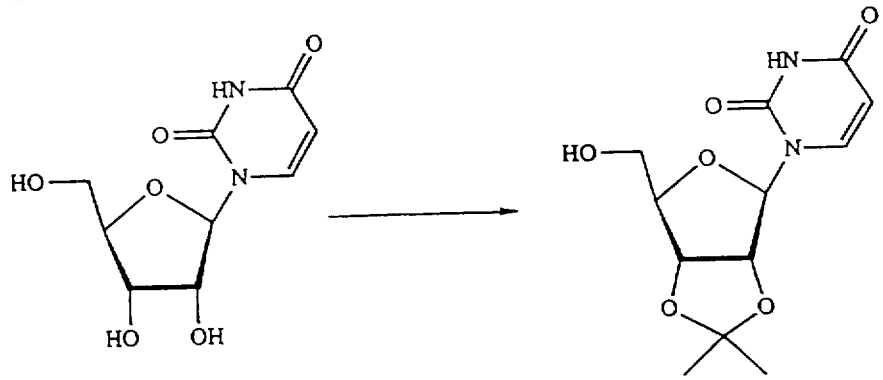

Under Example 9; column 22, lines 31-52: The formula should appear as follows:

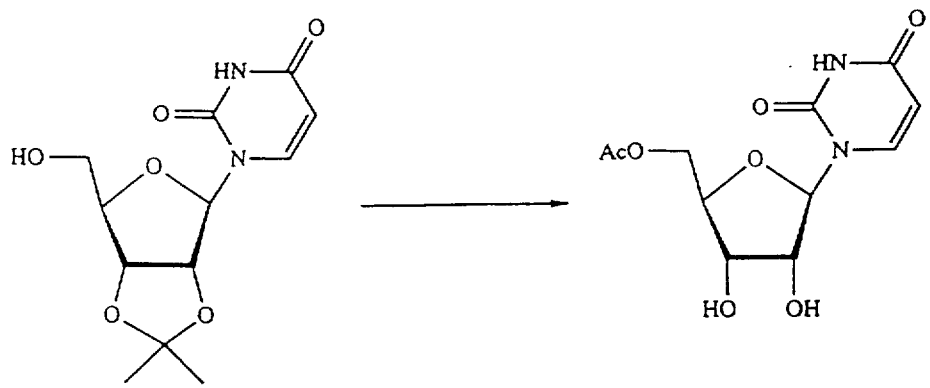

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 9; column 23, lines 2-21: The formula should appear as follows:

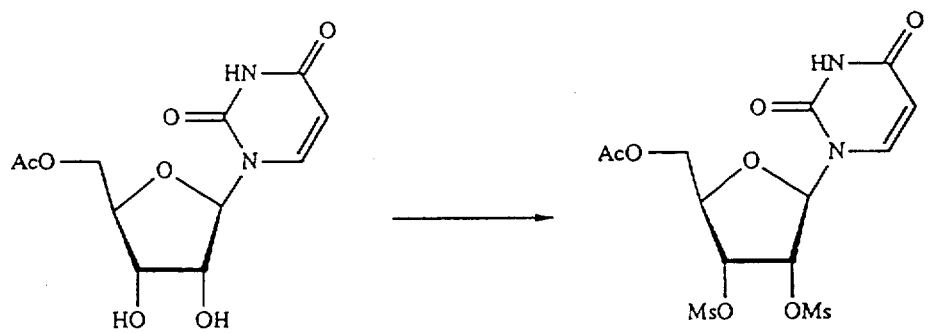

Under Example 9; column 23, lines 45-63: The formula should appear as follows:

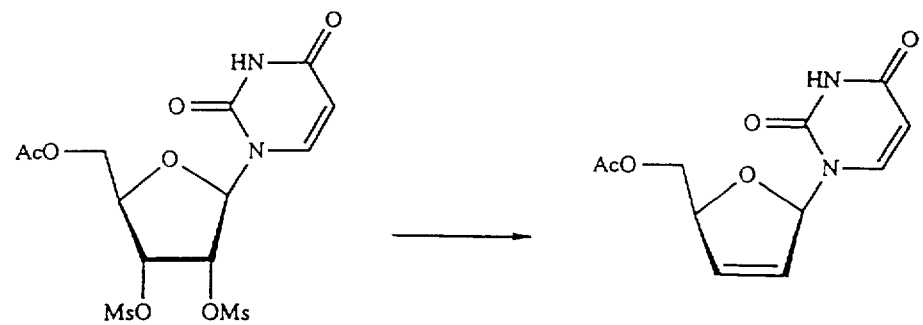

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 10; column 24, lines 22-38: The formula should appear as follows:

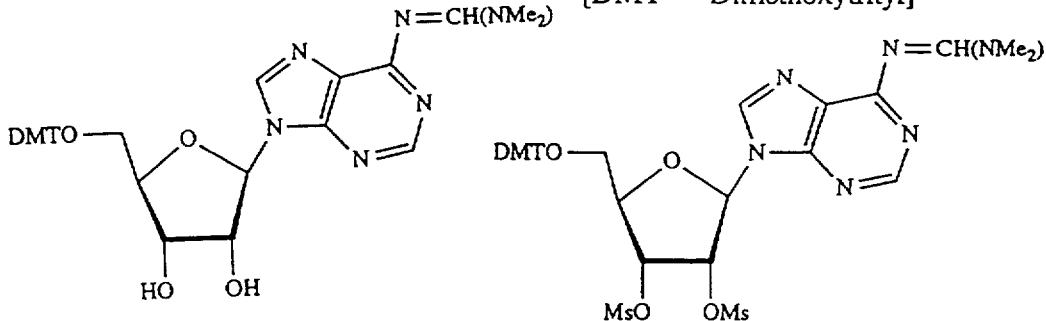

Under Example 10; column 24, line 43: After phenylmethyl delete "-" and replace with -- ] --.

Column 24, line 44: Before adenosine delete "]".

Column 24, line 56-57: Change "(acetone-de, 200 MHz)" to read -- (acetone-$d_6$, 200 MHz) --.

Column 24, line 58: Change "1H" in both occurences to -- 1 H --.

Column 24, line 58: Change "3H" to -- 3 H --.
Column 24, line 59: Change "3H" to -- 3 H --.
Column 24, line 59: Change "1H" to -- 1 H --.
Column 24, line 60: Change "2H" to -- 2 H --.
Column 24, line 60: Change "4H" to -- 4 H --.
Column 24, line 60: Change "7H" to -- 7 H --.

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Under Example 10; column 24, line 61: Change "2H" to -- 2 H --.
Column 24, line 61: Change "1H" in both occurences to -- 1 H --.

Column 24, line 62: Change "1H" to -- 1 H --.

Column 24, line 67: After for and before $C_{36}$ insert -- [ --.

Under Example 10; column 25, lines 6-20: The formula formula should appear as follows:

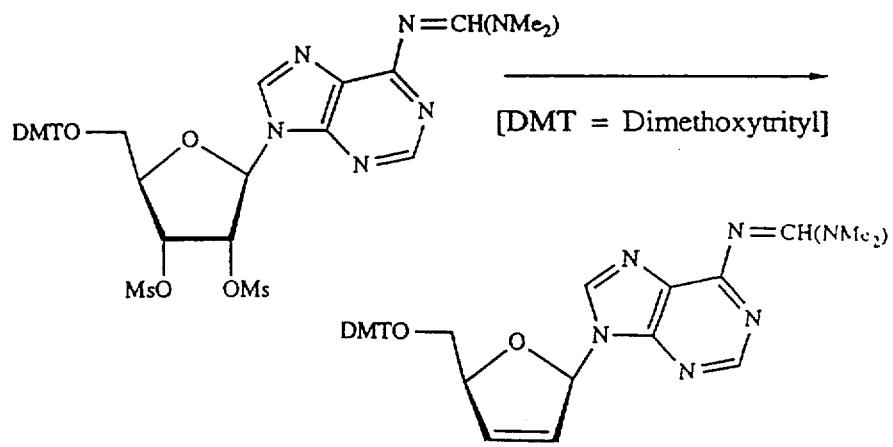

[DMT = Dimethoxytrityl]

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Column 25, line 36: change "1H" to --$^1$H--.

Under Example 10; column 25, line 37: Change "6H" to --6 H--.

Column 25, line 37: Change "1H" in both occurences to --1 H--.

Column 25, line 37: Change "3H" to --3 H--.

Column 25, line 38: Change "3H" to --3 H--.

Column 25, line 38: Change "1H" in both occurences to --1 H--.

Column 25, line 39: Change "1H" to --1 H--.

Column 25, line 39: Change "4H" to --4 H--.

Column 25, line 39: Change "7H" to --7 H--.

Column 25, line 40: Change "2H" to --2 H--.

Column 25, line 40: Change "1H" in both occurences to --1 H--.

Column 25, line 41: Change "1H" to --1 H--.

Claim 22; column 26, line 41: After is insert --5'-O- --.

UNITED STATES PATENT AND TRADEMARK OFFICE
CERTIFICATE OF CORRECTION

PATENT NO. : 5,410,033
DATED : April 25, 1995
INVENTOR(S) : Derrick L.J. CLIVE et al.

It is certified that error appears in the above-indentified patent and that said Letters Patent is hereby corrected as shown below:

Claim 23; column 26, line 43: After is insert -- 5'- O- --.

Claim 25; column 26, line 49: Before phenylmethyl] delete " - ".

Claim 28; column 26, line 55: Change "Uridine" to -- uridine --.

Signed and Sealed this

Third Day of October, 1995

Attest:

BRUCE LEHMAN

Attesting Officer

Commissioner of Patents and Trademarks